US008647306B2

(12) United States Patent
Schwirtz et al.

(10) Patent No.: US 8,647,306 B2
(45) Date of Patent: Feb. 11, 2014

(54) INJECTION DEVICE

(75) Inventors: Andreas Schwirtz, Vienna (AT);
Markus Csenar, Vienna (AT)

(73) Assignee: Pharma Consult Ges.m.b.H & Co Nfg KG (AT)

( * ) Notice: Subject to any disclaimer, the term of this patent is extended or adjusted under 35 U.S.C. 154(b) by 141 days.

(21) Appl. No.: 12/999,551

(22) PCT Filed: Jun. 16, 2009

(86) PCT No.: PCT/AT2009/000239
§ 371 (c)(1),
(2), (4) Date: Dec. 16, 2010

(87) PCT Pub. No.: WO2009/152542
PCT Pub. Date: Dec. 23, 2009

(65) Prior Publication Data
US 2011/0125100 A1    May 26, 2011

Related U.S. Application Data

(60) Provisional application No. 61/184,044, filed on Jun. 4, 2009.

(30) Foreign Application Priority Data

Jun. 16, 2008    (AT) .................................. A 958/2008

(51) Int. Cl.
*A61M 5/32*    (2006.01)
(52) U.S. Cl.
USPC ............ 604/192; 604/130; 604/134; 604/187
(58) Field of Classification Search
USPC ......... 604/130, 131, 134–137, 139, 156, 157, 604/187, 192, 197–199, 110, 200, 201
See application file for complete search history.

(56) References Cited

U.S. PATENT DOCUMENTS

| 4,031,893 A | 6/1977 | Kaplan et al. |
| 4,850,968 A | 7/1989 | Romano |

(Continued)

FOREIGN PATENT DOCUMENTS

| DE | 3872122 T2 | 2/1993 |
| DE | 19925904 C1 | 2/2001 |

(Continued)

OTHER PUBLICATIONS

International Search Report, PCT/AT2009/000239, dated Nov. 20, 2009.

*Primary Examiner* — Kami A Bosworth
(74) *Attorney, Agent, or Firm* — Lerner, David, Littenberg, Krumholz & Mentlik, LLP

(57) ABSTRACT

The invention relates to an injection device (1), which comprises a support housing (2), an activating sleeve (9), a cartridge (3) containing a medicine (14), a first drive unit (4), a safety device (5), a needle arrangement (6), a needle protection element (7) and a second triggerable drive unit (8), whereby the latter moves the needle protection element (7) from the non-effective position into the position covering one needle end (21) of a cannula (20). The support housing (2) is surrounded over most of its longitudinal extension between its distal and proximal end (11, 12) by the activating sleeve (9), whereby the needle protection element (7) with the second drive unit (8) cooperating therewith is arranged radially between the support housing (2) and the activating sleeve (9), as viewed in axial cross section.

26 Claims, 15 Drawing Sheets

(56) References Cited

U.S. PATENT DOCUMENTS

| | | |
|---|---|---|
| 5,295,965 A | 3/1994 | Wilmot |
| 5,658,259 A | 8/1997 | Pearson et al. |
| 6,767,336 B1 | 7/2004 | Kaplan |
| 7,074,211 B1 | 7/2006 | Heiniger et al. |
| 7,566,324 B2 | 7/2009 | Hommann et al. |
| 7,744,565 B2 | 6/2010 | Heiniger et al. |
| 2006/0184134 A1 | 8/2006 | Heiniger et al. |
| 2006/0270984 A1 | 11/2006 | Hommann |
| 2007/0078382 A1 | 4/2007 | Hommann et al. |
| 2008/0023346 A1* | 1/2008 | Vonderwalde ............... 206/210 |
| 2008/0215001 A1 | 9/2008 | Cowe |

FOREIGN PATENT DOCUMENTS

| | | |
|---|---|---|
| EP | 0307367 A2 | 3/1989 |
| RU | 2181057 C2 | 4/2002 |
| WO | 9714455 A1 | 4/1997 |
| WO | 2005035029 A1 | 4/2005 |
| WO | 2005044345 A1 | 5/2005 |
| WO | 2005113039 A1 | 12/2005 |
| WO | 2007026163 A1 | 3/2007 |

* cited by examiner

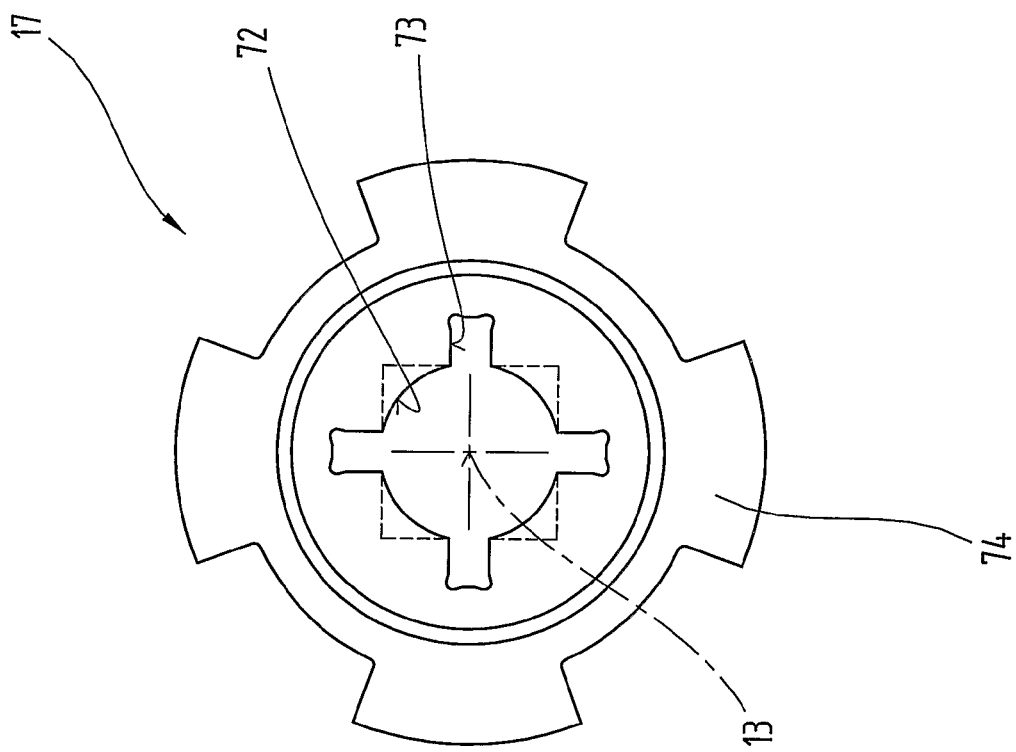

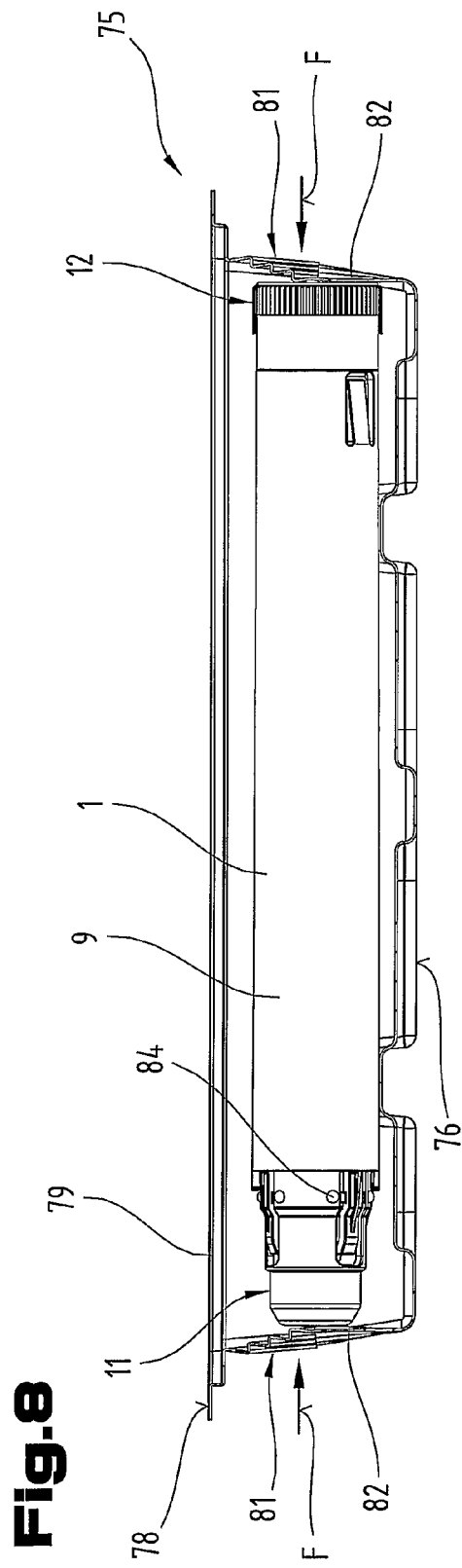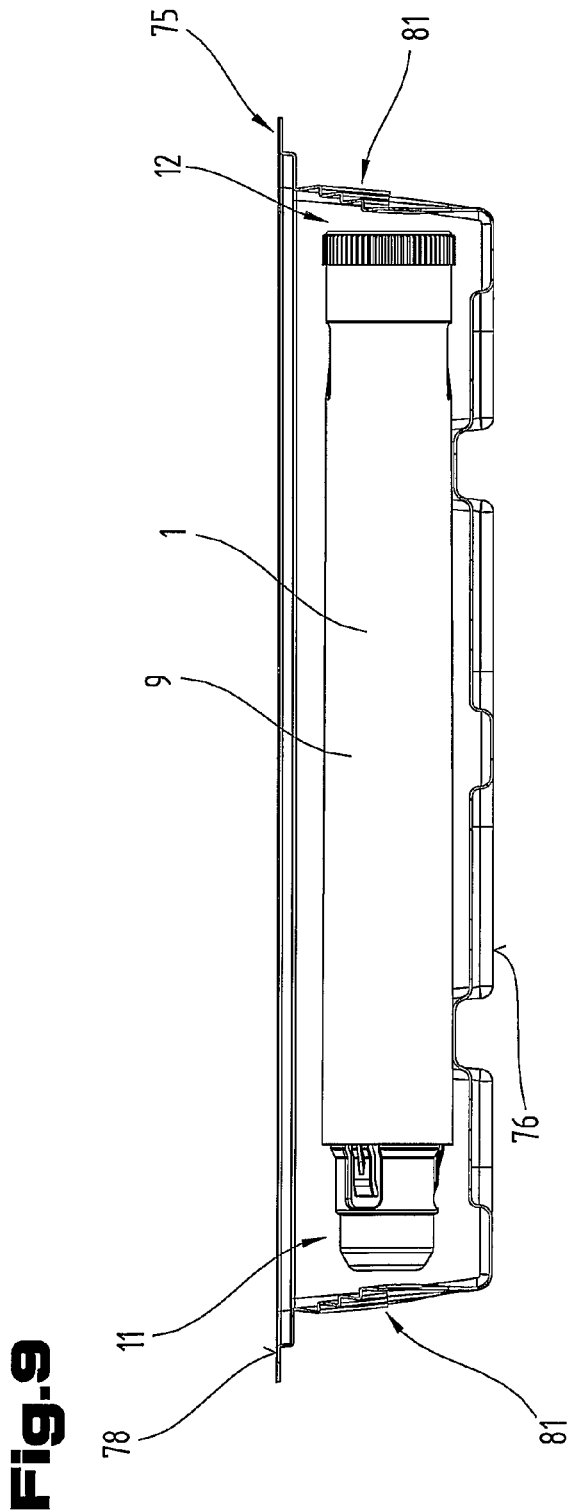

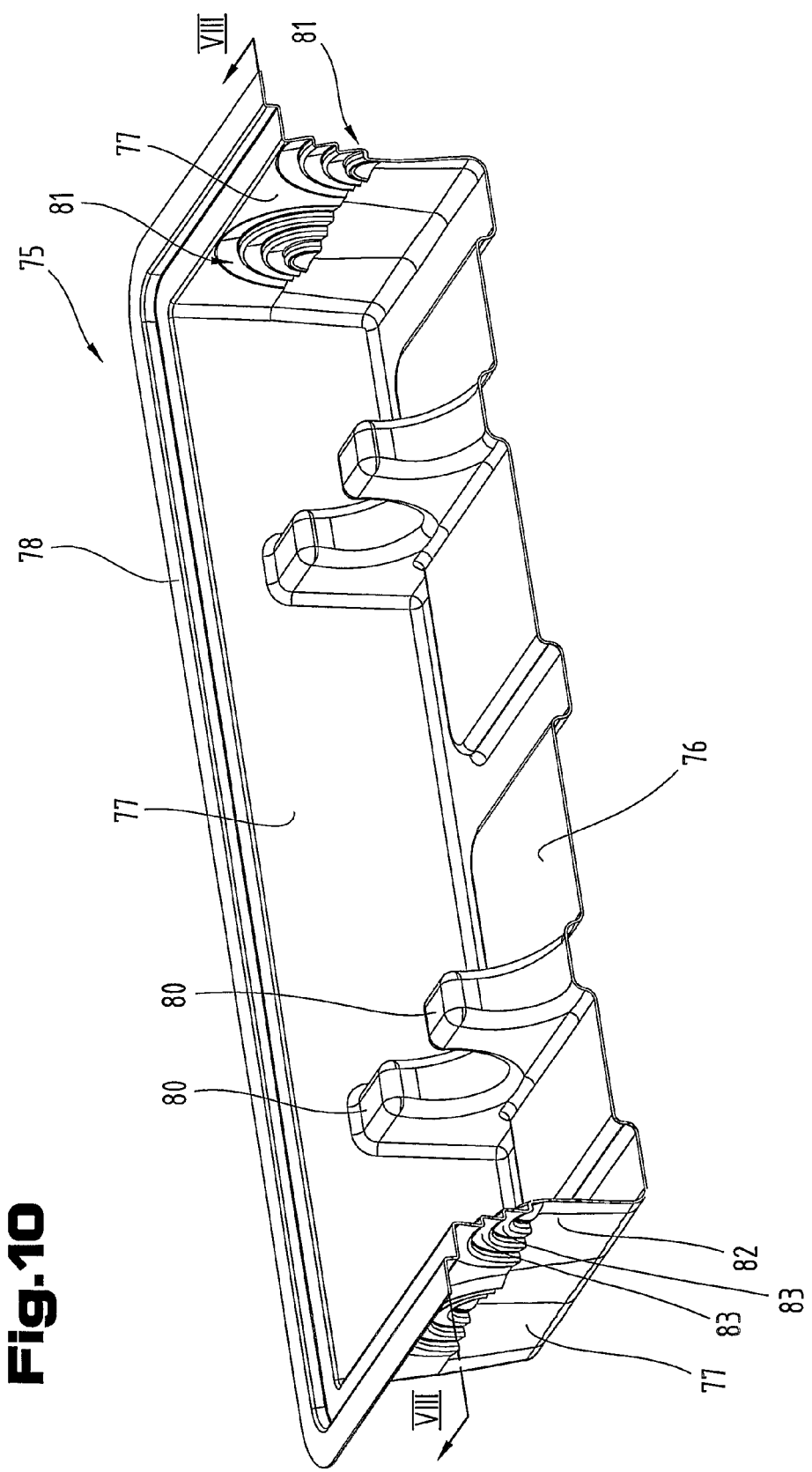

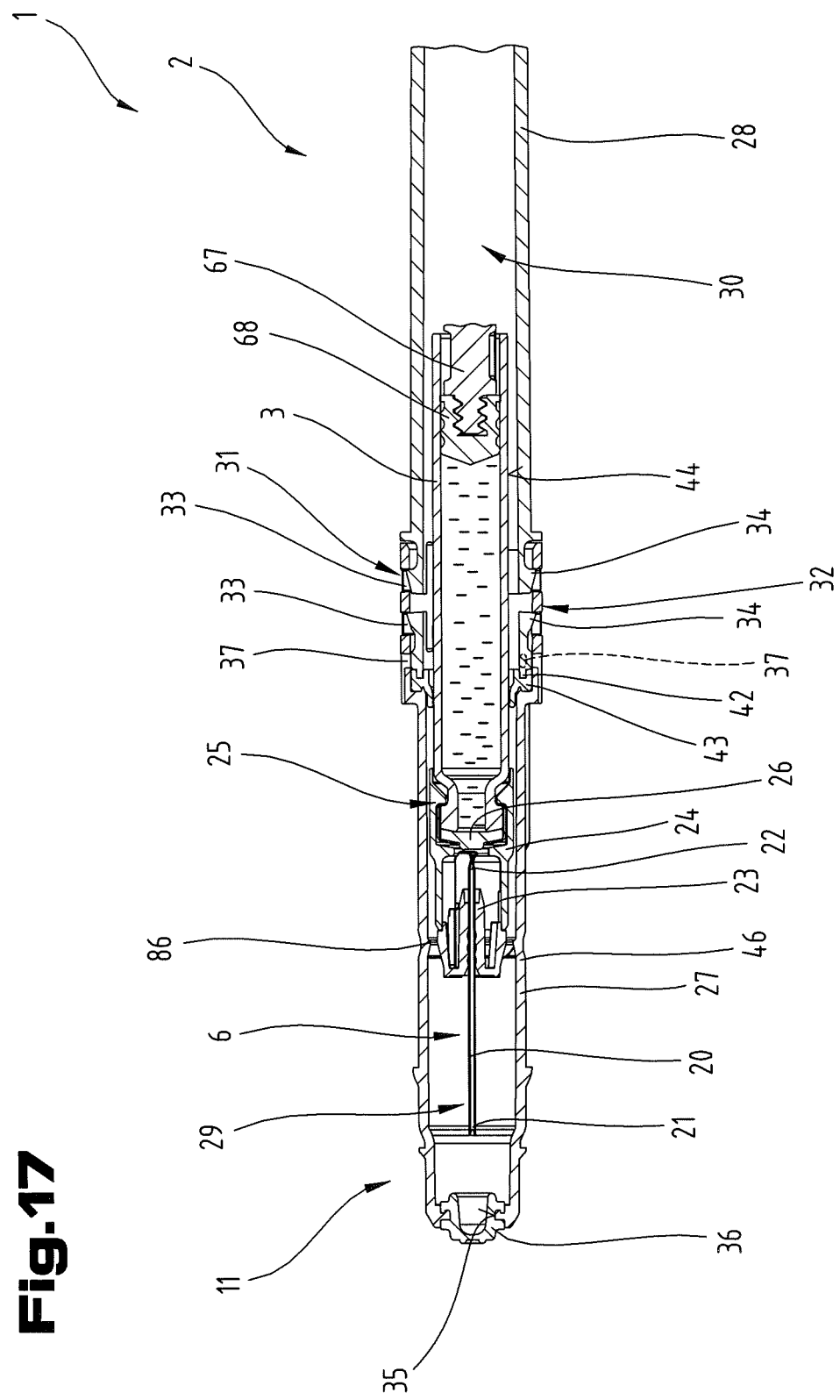

US 8,647,306 B2

INJECTION DEVICE

CROSS REFERENCE TO RELATED APPLICATIONS

The present application is a national phase entry under 35 U.S.C. §371 of International Application No. PCT/AT2009/000239, filed Jun. 16, 2009, published in German, which claims the benefit of Austrian Patent Application No. A 958/2008, filed Jun. 16, 2008, and U.S. Provisional Patent Application No. 61/184,044, filed Jun. 4, 2009. The disclosures of said applications are incorporated by reference herein.

The invention relates to an injection device, in particular an autoinjector, for administering a medicine.

From WO 2005/044345 A1 an autoinjector device is known, which comprises an ampoule housing on its outside, inside which a release sleeve is mounted displaceably in axial direction. In this case the inner release sleeve, as viewed in radial direction, is designed over the most part of its overall length to bear against the outer ampoule housing. Inside the release sleeve the ampoule is arranged with a needle screwed onto it and associated drive springs. The needle protection for the needle is arranged inside the release sleeve and is displaceable relative to the latter in axial direction. The release sleeve is aligned in its initial position with its front end approximately flush with the front end of the needle protection. In this case the needle is still arranged in a protected position inside the injection device. On applying the injection device to the injection site the release sleeve is pushed into the ampoule housing and in this way also ensures a displacement of the coupling element in axial direction to the rear end of the ampoule housing, whereby the release head is coupled with the needle protection element such that in the case of separately pushing in the release head the needle protection element is pushed out of a position securing the ampoule carrier and the ampoule carrier is pushed by the needle pushing spring in the pushing out direction of the injection needle. The needle pushing spring is supported on the one hand on the ampoule carrier and on the other hand on the ampoule housing or the ampoule carrier feed device. By means of the needle pushing spring the needle is moved together with the ampoule out of the injection device, whereby the injection is made in the region of the intended injection point. In this way at the same time the syringe holder is pushed into a front position, whereby the needle protection spring arranged between the syringe holder and the needle protection is tensioned and compressed. By means of the needle pushing spring the ampoule carrier in the ampoule carrier guide is pushed so far to the front, that locking elements are opposite the recesses provided on the inside of the ampoule carrier guide. In this position the radially outwards pretensioned locking element are pushed into said recesses, whereby the stopper holder is released and detached from the ampoule carrier. The injection spring tensioned between the rear end of the ampoule carrier and the plunger can then relax, whereby the stopper is pushed into the ampoule. In this way the substance contained in the ampoule is displaced and administered through the extended needle. If the entire injection device is removed from the injection site after performing the injection, the needle protection pretensioned by the tensioned needle protection spring in the direction of the injection needle is pushed to the front out of the injection device over the needle. In this embodiment the release sleeve is arranged inside the ampoule housing, whereby the actual release and activation is performed by the release head to be activated at right angles to the longitudinal axis.

WO 2005/113039 A1 describes an autoinjector for administering a medicine, which comprises fixed support housing with an inner and outer housing wall in the region of the distal end. The support housing contains the drive unit, the storage container for the medicine and the needle arrangement. The proximal end of the needle is in continual flow connection with the inner chamber of the storage container and thus with the medicine. Furthermore, the automatic injection device comprises a needle protection element which is displaceable in the direction of the longitudinal axis, which is guided between the inner and outer housing wall of the support housing. An additional drive unit is assigned to said sleeve-like needle protection element, in order after release to move the latter into the covering position of the needle. In addition, on the outside of the support housing a grip can be provided to improve handling. At the end opposite the needle—i.e. the proximal end—a release device is arranged for releasing the first drive unit. In this case the release movement is performed by a sliding movement in perpendicular direction in relation to the longitudinal axis. After the transverse displacement and the unlocking of the restraining device the first drive unit is activated, whereby the piston together with the storage container is moved so far in the direction of the distal end, until a stop of the storage container facing the proximal end reaches a stop of the inner housing wall of the support housing. At the same time as this longitudinal displacement the needle protection element is also released, which is moved in this way until applied to the administration site of the medicine. After administering the medicine and removing the entire injection device owing to the already activated additional drive device an additional forwards movement of the needle protection element is performed until the needle is completely covered.

From U.S. Pat. No. 6,767,336 B1 an automated injection device is known for administering a medicine, which comprises a support housing in which the drive unit, the storage container for the medicine and the needle arrangement are arranged. Via the cannula of the needle arrangement an elastically deformable and penetrable protection element is passed through, which is connected to the needle holder. The needle holder supports the needle and is coupled to a storage container for the medicine at its distal end. The cannula is thus continually in flow connection with the inner chamber and thereby with the medicine. In the region of the distal end on the support housing a needle protection element is mounted longitudinally displaceably to which a further driving means is allocated. Starting from the proximal end of the support housing a triggering sleeve is assigned thereto and the latter mounts the support housing at least in part. A safety element is assigned to the first drive unit in order to avoid unwanted triggering. The triggering of the needle protection element or its driving means is performed during the relative displacement of the medicine store together with the needle arrangement arranged thereon. Both the triggering sleeve and the needle protection element are arranged closely together and behind one another in axial direction on the common support housing.

WO 2005/113039 A1 describes an autoinjector for administering a medicine, which comprises a fixed support housing with an inner and outer housing wall in the region of the distal end. The support housing contains the drive unit, the storage container for the medicine and the needle arrangement. The proximal end of the needle is in continual flow connection with the inner chamber of the storage container and thus with the medicine. Furthermore, the automatic injection device comprises a needle protection element which is displaceable in the direction of the longitudinal axis, which is guided between the inner and outer housing wall of the support housing. An additional drive unit is assigned to said sleeve-like needle protection element, in order after releasing to move the latter into the covering position of the needle. In addition on the outside of the support housing a grip can be provided to improve the handling. At the end opposite the needle—i.e. the proximal end—a releasing device is arranged for releasing the first drive unit. In this case the releasing movement is performed by a sliding movement in perpendicular direction in relation to the longitudinal axis. After the transverse displacement and the unlocking of the restraining device the first drive unit is activated, whereby the piston together with the storage container is moved so far in the direction of the distal end, until a stop of the storage container facing the proximal end reaches a stop of the inner housing wall of the support housing. At the same time as this longitudinal displacement the needle protection element is also released, which is moved until applied against the administration site of the medicine. After administering the medicine and removing the entire injection device owing the already activated additional drive device an additional forwards movement of the needle protection element is performed until the needle is completely covered.

From EP 0 307 367 B1 and DE 38 72 122 T2 an injection device is known for administering a medicine, in which the medicine can be taken in by drawing up into the injection cylinder. A safety device for a needle protection element arranged on the outer side of the injection cylinder is activated by means of a conical part on the piston rod. When injecting or administering the medicine, the safety device is triggered by the conical part, whereby under the effect of spring force the outerlying needle protection sleeve is displaced along the injection cylinder until the needle projecting over the injection cylinder is covered.

From U.S. Pat. No. 5,295,965 A an automated injection device is known for administering a medicine, in which the outer casing is a needle protection sleeve. The latter extends from the distal end facing the patient up to the proximal end and can be activated there by a cap-like triggering sleeve. For the activation a safety pin arranged in the region of the proximal end is released, which pin secures the first drive unit until released by the cap-like triggering sleeve. After the removal of the safety pin the sleeve-like triggering sleeve can be moved relative to the support housing and the needle protection sleeve, whereby both the first drive unit and the needle protection sleeve are triggered. The needle protection sleeve is in turn allocated its own spring device by which the latter is moved into a position covering the needle.

From U.S. Pat. No. 5,658,259 A and EP 0 956 058 B1 a further automated injection device is known for administering a medicine from a cartridge. For this the cartridge with the medicine is arranged inside a support housing, whereby the cartridge is further allocated a first drive unit for its activation and administering a medicine. Inside the support housing a needle protection sleeve is arranged which can be triggered by the longitude displacement of the needle support, which is also allocated an adjusting element. The needle protection sleeve is held inside the support body by means of a detent connection until its release by the displaced needle support. After administering the medicine the needle protection sleeve covers the end of the needle projecting over the autoinjector.

U.S. Pat. No. 4,031,893 A describes a further autoinjector, in which in a common support housing the triggerable drive unit and the medicine container is mounted with the needle arrangement placed thereon. The drive unit is in turn secured against unintentional release by a safety element. The support housing is surrounded on the outside by a sleeve-like component, which is coupled at its proximal end to an additional triggering sleeve. The triggering sleeve after the removal of the safety cap with the safety pin triggers the drive unit, whereby the medicine container is displaced together with the needle arrangement in the direction of the distal end. The cannula which is in continual flow connection with the inner chamber of the medicine container is surrounded by an elastically deformable protective sleeve, which is supported on the inside of the distal end of the support housing. During the forwards movement the cannula penetrates the elastically deformable protection sleeve and exits the support housing for the injection. The elastically deformable needle protection sleeve after the completion of the injection process causes a restoring of the needle arrangement together with the medicine container into the interior of the support housing.

The underlying objective of the invention is to create an injection device, in particular an autoinjector, which in a simple operation provides a high degree of operational safety, in particular improved needle protection. Furthermore, a method for sterilisation is also described in which at least the entire needle arrangement remains reliably sterilised even during a long storage period.

Said objective of the invention is achieved in that the needle protection element with the second drive unit cooperating therewith, as viewed in axial cross section, is arranged radially between the support housing and the activating sleeve, and in that the support housing has a front and a rear support housing part with a front and rear holding space respectively, and the two support housing parts can be coupled together in a connecting section by a coupling device in the direction of the longitudinal axis in two different longitudinal positions in a first and a second coupling position.

The surprising advantage resulting from the features of the claims is that the activating sleeve also mounts the drive unit assigned to the needle protection element, whereby manipulation for possible later use is reliably avoided. Furthermore, in this way even for the entire storage in the storage position manipulation of the drive units and needle protection element is avoided. In addition however, additional protection of all of the internal components is achieved by almost completely covering by the activating sleeve. The simple operation also means that incorrect handling is practically impossible and no additional displacement movements or triggering movements are necessary to initiate the administration of the medicine. A further advantage is that the activating and operating sleeve after its release by the safety device can be easily brought up to the body part receiving the medicine by the user in a one-handed operation at the same time as the entire injection device and by supporting the support housing of the injection device on said body part and by suitable pressure loading a relative displacement of the activating sleeve opposite the support housing can be achieved. In this way the administration process of the medicine is initiated and performed. In this way the entire injection device is prepared simply by removing the safety cap of the safety device for the following administering process and the medicine is administered automatically with a further single pressure movement introduced via the activating sleeve onto the corresponding body part. Furthermore, it is also advantageous, as by separating the support housing into two mutually displaceable support housing parts different operating states can be achieved, which are significant as part of the sterilisation and the following period of storage.

An embodiment according to the claims is also advantageous as thus an additional guide is formed between the support housing parts to be coupled together, whereby at the same time in this area predefined coupling positions can be created.

By means of the embodiment according to the claims it is possible in the first coupling position to achieve a defined positioning of the two support housing parts relative to one another and also to provide the option of external access in this position to the front support housing part.

In a further embodiment according to the claims only one direction of movement of the two support housing parts relative to one another is allowed, but unintentional separation, caused for example by vibrations and shocks etc., is reliably prevented.

A development according to the claims is also advantageous, as in this way the support housing at its distal end also allows penetration through the sealing stopper, and thereby a sterile sealing of the front holding chamber in connection with the front support housing part is ensured during the entire storage period.

In the embodiment according to the claims it is an advantage that at a predetermined point access required for the subsequent sterilisation is provided to the front holding chamber in order to be able to sterilise the needle arrangement contained and mounted therein even with an already pre-mounted injection device.

By means of the development according to the claims a predefined stop area can be created on the one hand for the sealing element and on the other hand for the support of the second drive unit.

By means of the embodiment according to the claims after completing the sterilisation a clear and reliable sealing of the sterilised front holding chamber can be performed. Furthermore, the circumferential sealing element can also be used as a damping holder for the cartridge with the medicine mounted in the support housing. In this way impact and shocks from the outer activating sleeve can be dampened or completely reduced and eliminated towards the cartridge containing the medicine.

An embodiment according to the claims is also advantageous, as in this way for gassing during the ETO sterilisation only a predefined inner chamber has to undergo sterilisation.

According to an embodiment described in the claims, with an already pre-mounted injection device between the individual components access can still be provided to the front holding chamber for the subsequent sterilisation.

In this case an embodiment according to the claims has proved to be advantageous, as with a short displacement movement between the two support housing parts after the sterilisation a perfect seal can be achieved even for longer storage periods.

In an advantageous development according to the claims between the activating sleeve and the support housing only pushing into one another and over one another is allowed, but the unintentional separation of the two parts from one another is reliably prevented. In this way a very high degree of operational reliability is achieved and manipulation is virtually unnecessary.

A development according to the claims is also advantageous, as in this way a clearly predefinable control area is formed and after a predeterminable relative displacement movement between the activating sleeve and the support housing the needle protection element is released or activated. The latter is adjusted by means of the second drive unit cooperating therewith into a position covering the cannula after use.

According to the claims during the storage position a distinct securing in position is achieved between the needle protection element and the support housing. This locking can be triggered by a simple pivot movement of the lever element, whereby for this a relative longitudinal displacement is required between the support housing and the activating sleeve, whereby in cooperation with the stop surface formed on the activating sleeve the rib-like lever element is adjusted and thus the needle protection element released.

In the development according to the claims a repeat restoring and associated therewith a repeat release of the already used needle tip of the cannula is prevented.

Also an embodiment according to the claims is possible, as hereby additionally the needle protection element is fixed mechanically between the support housing and the activating sleeve.

The embodiment according to the claims allows a stop delimitation for the forwards movement of the needle protection element in the covering position. In this way the adjusting forces of the driving means of the second drive unit can be selected to be slightly higher in order to obtain a perfect covering position each time.

An embodiment according to the claims is advantageous, as in this way a premanufactured unit can be created, which can be arranged or held on the cartridge. This entire needle arrangement is set up so that the needle tip facing the cartridge or the cartridge seal does not penetrate the cartridge seal during the entire storage position, and thus no medicine stored in the cartridge can be discharged. The flow connection between the cannula and the interior of the cartridge is only formed during the injection procedure.

Furthermore, also an embodiment according to the claims is advantageous, as in this way the needle support can be held in a clear fixed position relative to the guiding element and only after a predefinable adjustment of the cartridge relative to the support housing can the flow connection be formed between the cartridge and the inner chamber of the cartridge.

However, an embodiment as described in the claims is possible, as in cooperation with a control cam only at a predeterminable point or after a predeterminable adjustment the injection process of the needle end is performed through the cartridge seal and thus access is provided to the medicine to be administered.

The embodiment according to the claims is advantageous as in this way by reducing the dimension in the region of the piston rod a greater spacing is achieved from the inner wall of the cartridge and thus in case of impact damage to the cartridge can be prevented.

Also a further embodiment according to the claims is advantageous, as thus with a clear short adjustment path between the activating sleeve and the support housing the injection procedure can be triggered, which is performed automatically after triggering or activating the drive unit.

An embodiment according to the claims is also advantageous, as thus during the relative longitudinal displacement of the entire needle unit with the cartridge on the one hand the moment of injection into the patient and on the other hand the formation of the flow connection with the inner chamber of the cartridge can be determined.

By way of the embodiment according to the claims it is possible firstly to achieve a secure injection of the cannula into the patient and only then provide access to the medicine. In this way prior to the injection of the cannula into the patient the medicine is prevented from exiting the needle unintentionally.

In a further embodiment variant according to the claims a high degree of operational safety of the entire injection device is achieved, as on activating the first drive unit, also the needle protection is activated for the position to be covered of the used cannula.

A development according to the claims is also advantageous, as thus in a single displacement movement there is a simultaneous release and in this way in the case of a possible malfunction prior to the delivery of the medicine also the covering of the needle tip projecting over the housing is performed reliably.

Furthermore, an embodiment described in the claims is also advantageous, as in this way a slim structure is possible and in addition a relatively precise longitudinal guiding of the needle protection element on the support housing can be achieved.

Also an embodiment as described in the claims is possible, as in this way a relative arrangement of the holding arms relative to the holding disc is achieved and in this way reciprocal jamming is reliably prevented. Furthermore, in this way an even more reliable effect of the entire safety device can be achieved for the first drive unit.

Also an embodiment according to the claims is advantageous as thus the external sterilisation of the assembly can be performed, without in this way after the sterilisation impurities entering the not yet completely sealed sterilised holding chamber around the needle arrangement.

Also a development according to the claims is advantageous as in this way also several such injection devices can be stored arranged next to one another. Furthermore, also the external sterilisation of the assembly is made possible without in this way after the sterilisation impurities being able to enter into the not yet completely sealed sterilised holding chamber around the needle arrangement.

Lastly however, also an embodiment described in the claims is possible, as thus a material is used which according to current standards provides a germ-free and sterile storage even over an extended storage period.

Moreover, the objective of the invention is also achieved independently of this by a method for sterilising the injection device according to the features described in the claims. The advantages resulting from the combination of features in the claims are that such an injection device can be premanufactured with all of its components and mounted so that with a minimum amount of effort a completely tightly sealed holding chamber can be formed within the injection device. By separating the support housing into the two support housing parts after the sterilisation by interrupting the flow connection accordingly and absolutely sterile state of the components provided for the injection can be ensured. This is achieved with the simplest of means without additional sealing elements being required.

Furthermore, the objective of the invention is achieved independently of this by a method for sterilising the injection device according to the features described in the claims. The advantages resulting from the combination of features in the claims are that such an injection device can be premanufactured with all of its components and mounted so that with a minimum amount of effort a completely tightly sealed holding chamber can be formed within the injection device. With this injection device the entire needle arrangement and the inner chamber surrounding the needle arrangement can be sterilised, whereby over the entire storage period this sterile state can be maintained reliably. This is achieved with the simplest of means without additional sealing elements being required.

Furthermore, a procedure according the features described in the claims is advantageous as a completely sealed holding chamber is provided with a relatively short axial displacement of the front and rear support housing part onto one another.

A further advantageous procedure is described in the claims, whereby on the one hand access to the sterilised holding chamber is reliably prevented and in this locked position can be maintained even over a long storage period.

Also a procedure according the features described in the claims is advantageous as in this way the inner chamber to be sealed can be reduced in size and furthermore also a resilient support of the cartridge relative the support housing is also achieved.

Also a variant of the method according to the claims is advantageous as it allows external sterilisation of the assembly, without in this way after the sterilisation impurities re-entering into the not yet completely sealed sterilised holding chamber around the needle arrangement.

A procedure according to the claims is also advantageous as in this way also several such injection devices can be stored next to one another. Furthermore, also an external sterilisation of the assembly is possible, without in this way after sterilisation impurities reaching into the not yet completely sterilised holding chamber around the needle arrangement.

Lastly, a variant of the method according to the claims is also advantageous, as thus a material is used which according to current standards also allows a germ-free or sterile storage even over an extended storage period.

For a better understanding of the invention the latter is explained in more detail with reference to the following figures.

In a much simplified schematic representation:

FIG. 7 shows the holding disc of the safety device in plan view and in a simplified representation;

FIG. 8 shows the injection device of the invention according to FIG. 1 before or during sterilisation in a holding shell provided therefor, in cross section according to the lines VIII-VIII in FIG. 10;

FIG. 9 shows the injection device according to FIG. 8 in the holding shell in each coupling position after sterilising, in the completely sealed position;

FIG. 10 shows a partial section of the holding shell according to FIGS. 8 and 9 in a simplified view, without an injection device;

FIG. 17 shows an injection device showing the support housing with the cartridge and the needle arrangement inside the support housing in a second coupling position.

Figure 1:
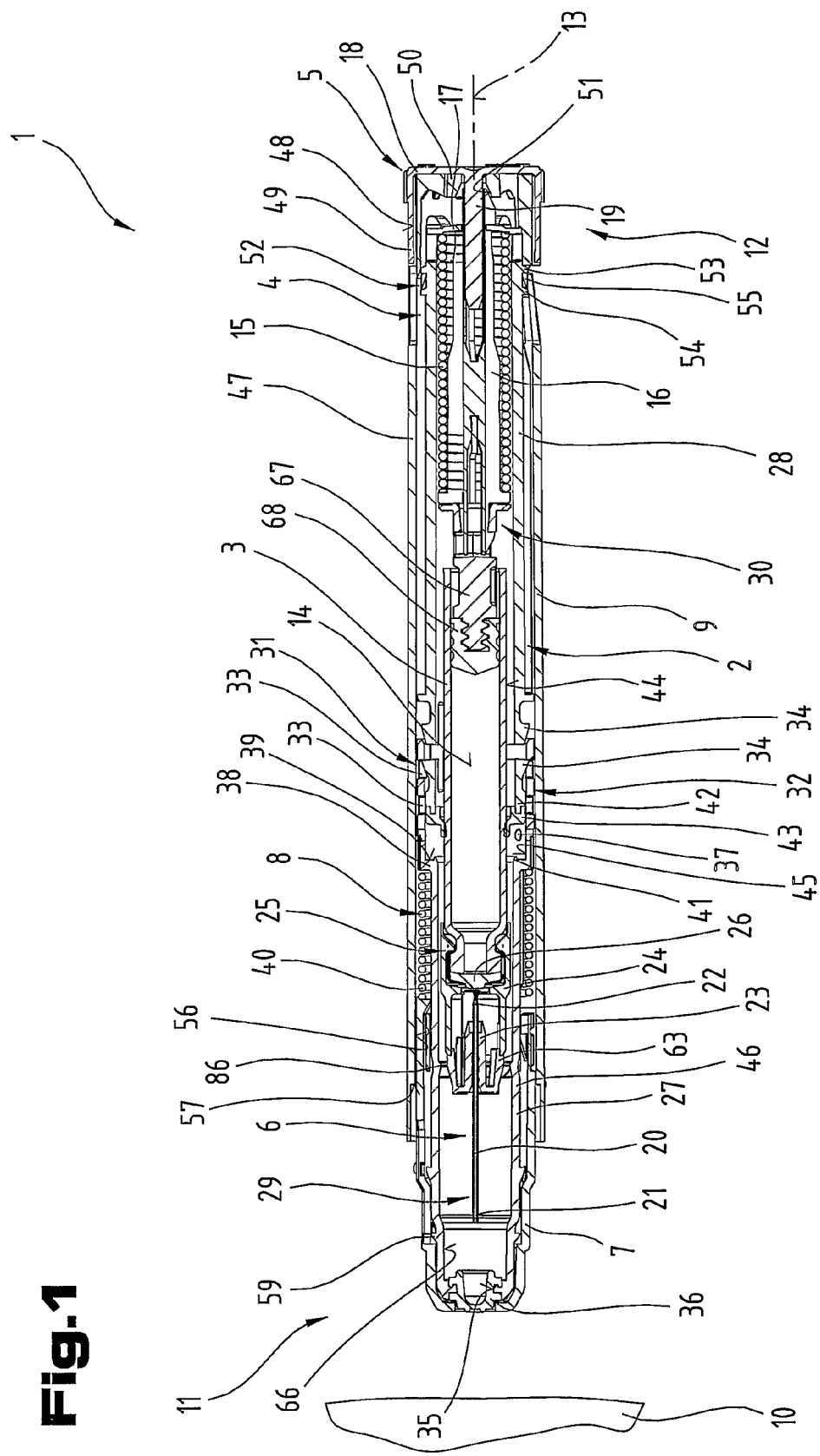
FIG. 1 shows an injection device designed according to the invention before the sterilisation of the holding chamber with the needle arrangement arranged therein, in axial cross section and simplified view.

Firstly, it should be mentioned that in the variously described embodiments the same parts are provided with the same reference numbers and the same component names, whereby the disclosures contained throughout the description can be transferred to the same parts with the same reference numbers or same component names. Also the details of position used in the description, such as e.g. top, bottom, side etc., relate to the figure currently being described and represented, and with a change in position should be adjusted accordingly to the new position. Furthermore, individual features or combinations of features from the shown and described different exemplary embodiments can represent in themselves independent, inventive solutions according to the invention.

All of the details relating to value ranges in the present description are defined such that they include any and all subranges, e.g. the specification of 1 to 10 includes all subranges starting from the lower limit 1 and including the upper limit 10, i.e. all of the subranges begin with a lower limit of 1 or more and end at an upper limit of 10 or less, e.g. 1 to 1.7 or 3.2 to 8.1 or 5.5 to 10.

In FIGS. 1 to 6 an injection device 1, in particular an autoinjector, is shown in simplified form in different operating positions. With such autoinjectors, which are used for the automatic administration of a medicine, a distinction is made between a storage position and an injection position, whereby between these two positions automated adjustment and displacement procedures take place and the related administration of the medicine is performed.

The injection device 1 is composed of a plurality of components and can comprise a support housing 2, a storage container mounted therein such as a cartridge 3, a first releasable drive unit 4, which is in active connection with the cartridge 3, a safety device 5, a needle arrangement 6, a needle protection element 7 and a second drive unit 8 assigned to the needle protection element 7 and thus in active connection therewith and an activating sleeve 9.

The injection device 1 i.e. the support housing 2 comprises a distal end 11 to be applied to the living being such as a patient 10 and a proximal end 12 averted therefrom, whereby a longitudinal axis 13 extends between the two ends 11, 12. Furthermore, in the description of the position front and rear is used and thereby the front is allocated to the distal end 11 and rear to the proximal end 12. The holding container for a medicine 14 is formed here by the cartridge 3, in which the medicine 14 or the active ingredient to be administered or injected is already stored during the storage position and is ready to be administered. The cartridge 3 is thereby mounted in the support housing 2 and surrounded by the latter. The cartridge 3 is a conventional packaging for medicine 14, whereby the amount of medicine 14 held therein can be adjusted to the respective application. Furthermore, in a known manner the first triggerable drive unit 4 is assigned to the cartridge 3 at the end facing the proximal end 12 of the injection device 1 or is in active connection therewith.

The first drive unit 4 comprises a first driving means 15, which is secured by the safety device 5 against release until the user actively activates the injection device 1, in which the first drive unit 4 is released and thus the injection device 1 is triggered. By means of the safety device 5 thus the first drive unit 4 is secured in its position relative to the support housing unit 4 prior its activation for the injection procedure. The first drive unit 4, in particular the driving means 15 and the holding arms 16 allocated to the driving means 15 are mounted inside the support housing 2. The holding arms 16 engage in turn in a holding disc 17 arranged in the region of the proximal end 12 of the injection device 1, whereby a detailed description thereof is given in the following. The safety device 5 also comprises a safety cap 18 to prevent the unintentional triggering of the drive unit 4, whereby in its centre a safety pin 19 penetrating the holding disc 17 is arranged. The safety pin locks the holding arms 16 in radial direction in a known manner with respect to the longitudinal axis 13 and prevents up to the removal of the safety cap 18 together with the safety pin 19 a release of the holding arms 16 locked onto the holding disc 17 in radial direction of the longitudinal axis 13.

In the region of the distal end 11 the needle arrangement 6 is arranged directly before the cartridge 3. The needle arrangement 6 comprises in turn a cannula 20 or a hollow needle with needle ends 21, 22 spaced apart from one another in the direction of the longitudinal axis 13. The cannula is held in turn by a needle support 23 and is mounted in the latter. Both needle ends 21, 22 project respectively on both sides of the needle support 23.

The needle support 23 is coupled in turn via a guiding element 24 to a cartridge end 25 facing the distal end 11 or is connected therewith. For further details see also the following FIGS. 11 and 12. The cartridge 3 in turn has at the cartridge end 25 facing the distal end 11 a penetrable cartridge seal 26. The proximal needle end 22 facing the cartridge seal 26 is arranged by means of the needle support 23 on the guiding element 24 such that in the storage position of the injection device 1 the needle end 22 is arranged spaced apart from the cartridge seal 26. Thus firstly access to the inner chamber of the cartridge 3 to the medicine 14 is prevented. Furthermore, in the storage position of the injection device 1 both needle ends 21, 22 are arranged inside the support housing 2 and thus needle stick injuries are prevented. Furthermore, as explained in more detail in the following, the entire needle arrangement 6 is kept in a completely sterile state during the entire storage period prior to the specified use of administering the medicine 14.

The needle protection element 7, which is in active connection with the second drive unit 8, can be shifted by means of the latter from a non-effective position into a position covering the needle end 21, which projects after the injection procedure over the distal end 11 of the support housing 2. The triggering of the second drive unit 8 and the displacement of the needle protection element 7 are also described in detail in the following. The needle protection element 7 together with the second drive unit 8 is arranged in the region of the exterior of the support housing 2 and is supported at least partly on the latter.

The support housing 2 is also surrounded over the most part of its longitudinal extension between the distal end 11 and the proximal end 12 by the activating sleeve 9 described above and is mounted in the latter. In this case only the distal end 11 of the support housing 2 projects over the activating sleeve 9 in axial direction. Here the term "over the most part" of its longitudinal extension is defined such that the activating sleeve 9 extends in relation to the length of the support housing 2 over an longitudinal extension in a lower limit of at least 50% and an upper limit of up to 100%. In this case advantageous values of the longitudinal extension are at least 50%, preferably at least 60%, in particular at least 70%, preferably at least 80%, preferably at least 90%, particularly preferably at least 95%. As almost the entire support housing 2 is mounted by the activating sleeve 9 or arranged inside the latter the needle protection element 7 is arranged with the second drive unit 8 interacting therewith, as viewed in axial section, radially between the support housing 2 and the activating sleeve 9. In this way there can be no influence on the second drive unit 8 for its triggering or deactivation. The activating sleeve 9 can also be defined as a triggering sleeve. Furthermore, the latter is used not only for the function of activating or triggering the first drive unit 4 but also for the user to hold the entire injection device 1 and keep holding it in the same way during the whole administration process.

The support housing 2 comprises in turn a front and a rear support housing part 27, 28, whereby the front support housing part 27 faces the distal end 11 and thus the patient 10. The rear support housing part 28 is arranged closer to the proximal end 12. The two support housing parts 27, 28 delimit and define respectively a front and rear holding chamber 29, 30, and can be coupled together in a connecting section 31 arranged between the latter by a coupling device 32 in the direction of the longitudinal axis 13 in two different longitudinal positions, a first and a second coupling position.

FIG. 1 shows the first coupling position, in which the two support housing parts 27, 28 in relation to the second coupling position have a greater longitudinal extension in the direction of the longitudinal axis 13. Furthermore, it is also shown that in the connecting section 31 and the coupling device 32 arranged there the front support housing part 27 grips over the rear support housing part 28.

The coupling device 32 has on the two support housing parts 27, 28 cooperating locking elements 33, 34, which are designed such that the two support housing parts 27, 28 are locked in the two coupling positions in opposite movement directions. Here the term opposite movement direction is meant as locking which prevents the moving apart of the two support housing parts 27, 28 in the direction of the longitudinal axis 13, but allows moving towards one another from the first coupling position into the second coupling position.

Figure 3:
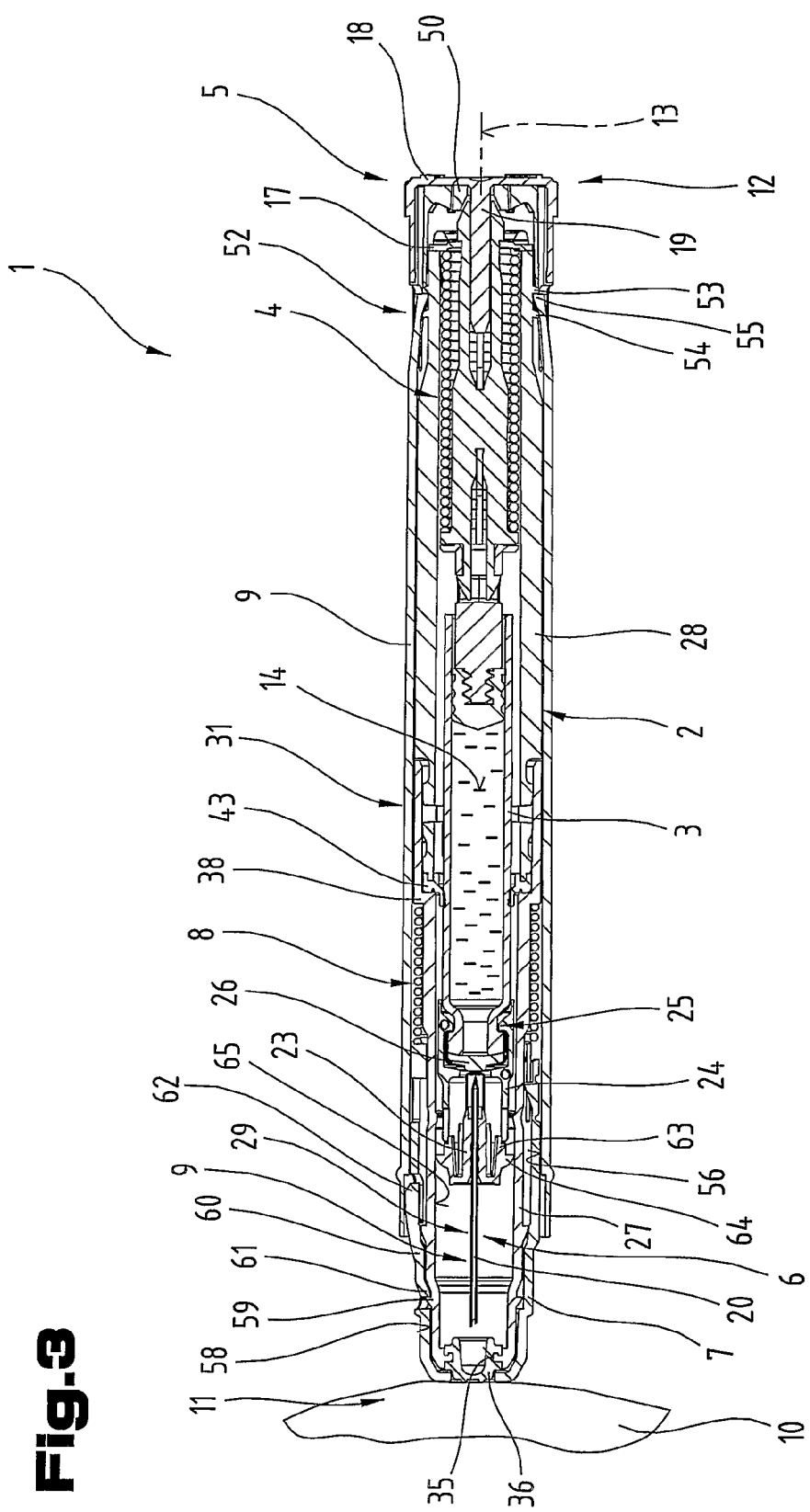
FIG. 3 shows the injection device according to FIGS. 1 and 2 in the already sterilised state, in axial cross section and simplified representation.

The first locking elements 33 of the coupling device 32 are for example formed in the region of the front support housing part 27 by recesses or openings in the wall of the front support housing part 27. Preferably, as viewed in axial direction for the two coupling positions several locking elements 33 arranged behind one another are provided. The locking element or further locking elements 34 of the coupling device 32 of the rear support housing part 28 can be formed by detent noses or detent projections engaging in recesses or openings, whereby preferably as viewed in the direction of the longitudinal axis 13 several of these locking elements 34 are provided. In the first coupling position, in which the two support housing parts 27, 28 have a greater longitudinal extension than in the second coupling position, only the front locking elements 34 are in engagement with the rear locking elements 33 of the front support housing part 27. The second coupling position is shown in FIG. 3 in a cross sectional plane rotated differently to FIG. 1. In this way in the second coupling position the two locking elements 34 of the rear support housing part 28 arranged behind one another come into engagement with the corresponding locking elements 33 of the front support housing part 37. Thus in both positions the distancing of the two support housing parts 27, 28 is prevented.

In the region of the distal end 11 the support housing 2 or the front support housing part 27 has an opening 35 allowing the passage of the needle end 21 of the needle arrangement 6. In this opening 35 a penetrable sealing stopper 36 is arranged in a position sealing the front holding chamber 25 relative to the outer environment.

The front support housing part 27 in connection section 31 with the rear support housing part 28 has at least one throughput 37, which allows access from the outside of the support housing 2 at least into the front holding chamber 29 with the needle arrangement 6 arranged therein. The throughput 37 is thus arranged or provided in the wall section of the front support housing part 27 gripping over the rear support housing part 28. Immediately adjacent to the throughput(s) 37 the connecting section 31 gripping over the rear support housing part 28 ends with a wall part 38 springing back to the longitudinal axis 13, which is preferably arranged in a plane aligned perpendicular to the longitudinal axis 13. Said wall part 38 has a face end 39 facing the rear support housing part 28, which is also arranged preferably in the plane aligned perpendicular to the longitudinal axis 13. On the wall part 38 also on the side averted from the rear support housing part 28 the second drive unit 8 is supported with a further driving means 40. The driving means 40 can in turn be formed by a pretensioned compression spring or similar spring element.

Furthermore, on the backspringing face end wall 39 of the wall part 38 a shoulder 41 designed to be wedge-shaped in axial cross section and continuous around the circumference can be arranged. The wedge-shaped tapering is in this case aligned in the direction of the rear support housing part 28.

On the rear support housing part 28 at its end 42 facing the front support housing part 27 a sealing element 43 designed to be continuous around the circumference is arranged or secured thereon. The sealing element 43 is preferably arranged on a face end side of the rear support housing part 28 and secured there. The sealing element 43 designed to be circumferential bears both against the external surface 44 of the cartridge 3 and an internal surface 45 of the front support housing part 27, in particular in the connecting section 31. This bearing preferably seals around the entire circumference on both surfaces 44, 45, whereby in the first coupling position of the two support housing parts 27, 28, the sealing element 43 is arranged spaced apart from the face end wall 39 of the wall part 38 or the shoulder 41 formed on the face end wall 39.

The front support housing part 27 comprises a casing 46 designed to be roughly cylindrical, which in the region of the distal end 11 comprises the opening 35 described above, which is sealed by the sealing stopper 36. The casing 46 is continuous and thus designed to seal up to the connecting section 31. In the latter only the throughputs 37 are provided, through which, in the first coupling position of the two support housing parts 27, 28, a flow connection is formed in the front holding chamber 29 of the front support housing part 27. In this way over the circumference, only one or even several of the throughputs 37 can be provided, which run from the outside of the front support housing part 27 into the front holding chamber 29. In this way in the first coupling position the front holding chamber 29 of the front support housing part 27 on the one hand is delimited in a sealing manner by the casing 46, the sealing stopper 36 arranged in the opening 35, the sealing element 43 and the cartridge 3 projecting into the front holding chamber 29 and a flow connection is provided simply via the throughput 37.

Independently of this it would also be possible however to make not only the front holding space 29 accessible for sterilisation via the throughputs 37, but also to provide access to the rear holding space 30. This could be achieved in that the sealing element 43, as viewed over the circumference, does not bear completely against the outer surface 44 of the cartridge 3. The support of the cartridge 3 on the rear support housing part 28 can be performed via individual support webs distributed around the circumference, which have not been shown in more detail. Furthermore, by means of the divided design of the support housing 2 into the front and rear support housing part 27, 28 a simple sterilisation can be performed by means of gas application and afterwards by means of a corresponding sealing process of the sterile inner chamber the latter can be maintained over a longer period.

In the second coupling position of the two support housing parts 27, 28 the sealing element 43 bears in a sealing manner against the face end wall 39 of the wall part 38 or the shoulder 41 arranged thereon. To obtain a better peripheral seal, the wedge-shaped shoulder 41 described above is provided, which pushes in axial direction into the sealing element 43 during its bearing thereon.

By means of the mutual displacement of the two support housing parts 27, 28 towards one another, the sealing element 43 is pushed past the throughput 37 and the front holding space 29 is completely sealed. Furthermore, the peripheral sealing element 43 can also be used as a damping holder for the cartridge 3 with the medicine mounted in the support housing 2. In this way impact and stress from the external activating sleeve 9 towards the cartridge 3 with the medicine 14 can be damped or completely reduced and absorbed.

Figure 5:
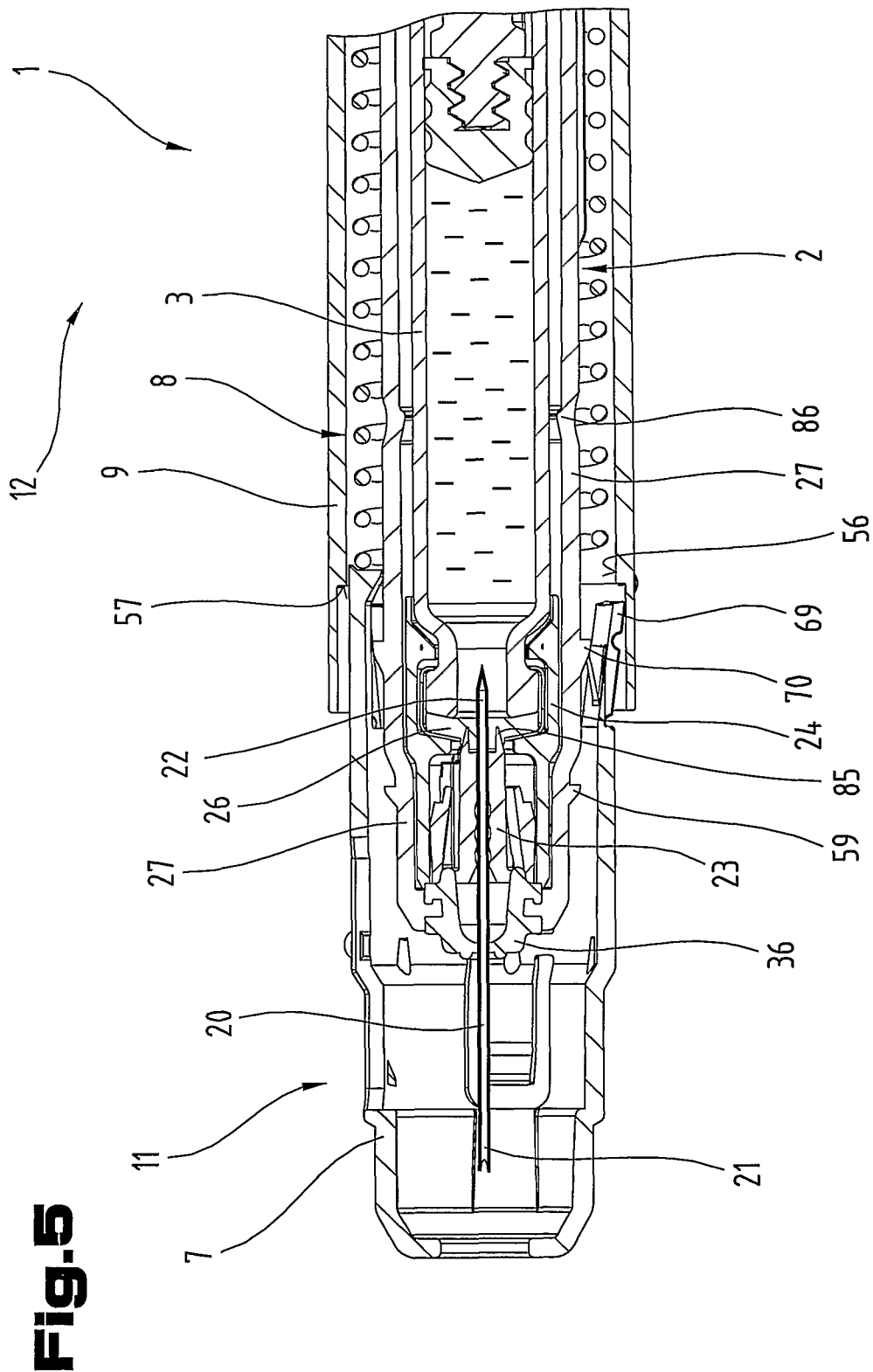
FIG. 5 shows the injection device according to FIGS. 1 and 4 in a position of the needle protection element covering the cannula, in axial cross section and simplified representation.
Figure 6:
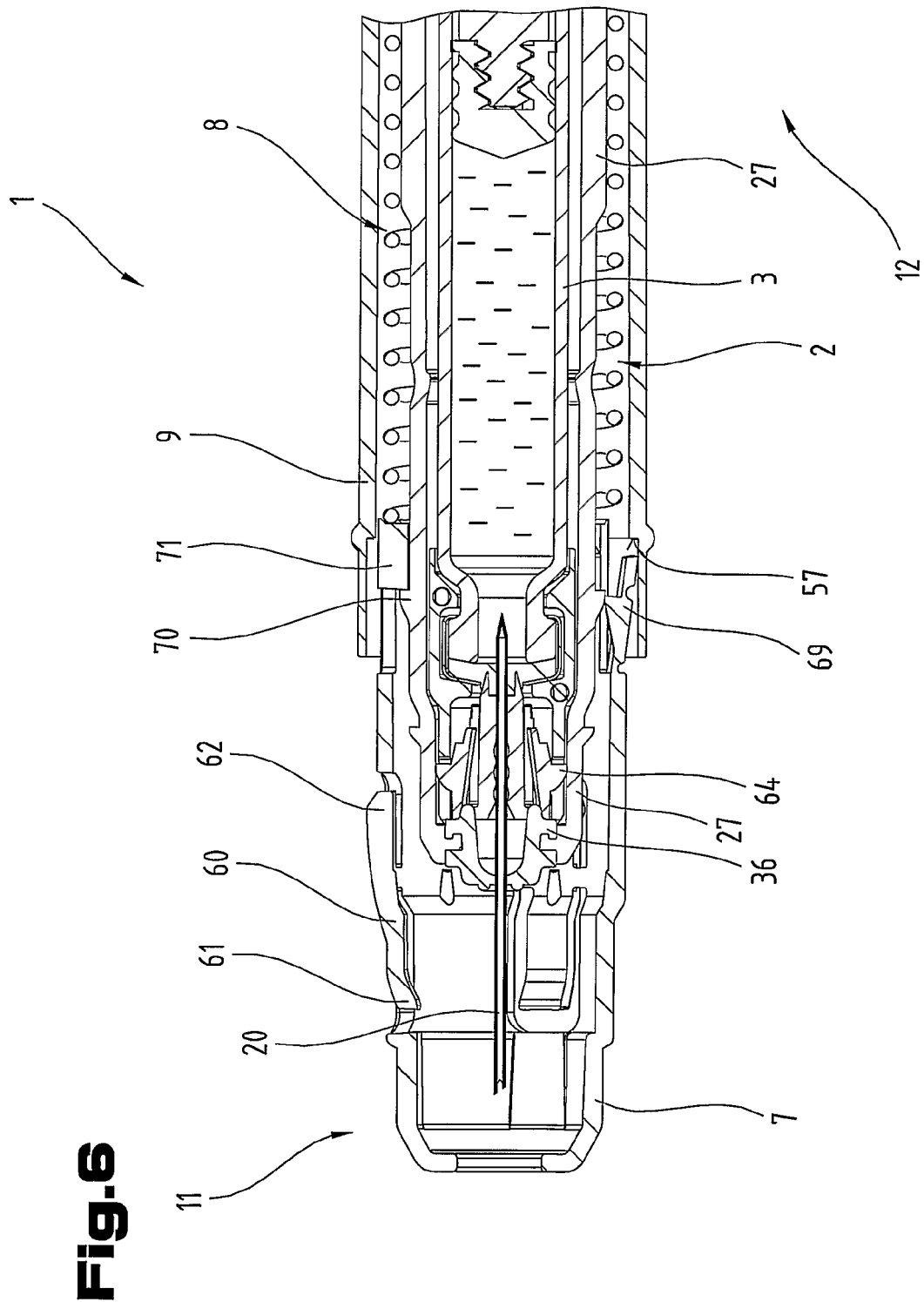
FIG. 6 shows the injection device according to FIG. 5, but in a different cross sectional plane.

A further damping device 86 can be seen from an overview of FIGS. 1 and 5. This is formed on the internal surface 45 of the support housing 2, in particular the front support housing part 27, as a flange projecting into the clear cross section or as a constriction of the casing 46. The arrangement is as viewed in axial direction in the storage position in the region or section of the needle support 23 or the guiding element 24. In a drop test the cartridge 3 or the needle support 23 and/or the guiding element 24 could thus be supported thereon and an unintentional further movement of the cartridge 3 in the direction of the distal end 11 could be stopped. The damping device 86 thus forms a mechanical resistance against an axial movement.

The access via the throughput 37 in the first coupling position is used for sterilising the front holding chamber 29 together with the needle arrangement 6 arranged therein. As during the sterilisation the cartridge 3 with the medicine 14 stored therein is already arranged inside the injection device 1, there are only a small number of serialisation options. Sterilisation under the effect of heat or radiation with electron beams should be avoided for these reasons, so as to avoid negatively affecting the medicine 14. In the present exemplary embodiment preferably gassing with ethylene oxide is performed via the throughput 37 arranged in the connecting section 31. The gassing can also be called ETO-gassing and is sufficiently well known. After the sterilisation process the two support housing parts 27, 28 are moved relative to one another from their first coupling position into the second coupling position, whereby, as already described, the circumferential sealing element 43 ensures the complete sealing of the front holding chamber 29 relative to the external environment. In this way the entire needle arrangement 6 and the cartridge seal 26 is sterilised on the side facing the front holding chamber 29 and remains in this state until the use or application of the injection device 1.

It is also possible that before the sterilisation is carried out by gassing the injection device 1 is completely surrounded by a casing, not shown in detail. In this case for example the casing is made from a paper-fleece-like fibrous material made of thermally welded fibres of high density polyethylene (HDPE). The paper-fleece-like fibrous material is sold for example by the company DuPont under the trade name TYVEK and has the property that the passage of the ethylene oxide required for the gassing is made possible, but the formation of germs and bacteria is reliably prevented. Thus for example the injection device 1 located in the first coupling position of the front end rear support housing part 27, 28 can be surrounded in a simple or also multiple arrangement by the casing. Subsequently, sterilisation by gassing is performed at a suitable location. Following the sterilisation in a separate procedure the two support housing parts 27, 28 are moved into the second coupling position, and thereby the front holding chamber 29 is fired in a sealing manner relative to the external environmental conditions, as already described in detail above. If several injection devices 1 are stored in a tray or holding shell described in more detail below and covered by a cover on the holding shell or surrounded by a casing, the tray can on the wall parts facing the two ends 11, 12 have easily deformable wall sections, which allow the pushing together of the two support housing parts 27, 28 against one another from the first coupling position to the second coupling position, without the tray getting damaged. This is described in more detail in FIGS. 8 to 10.

The activating sleeve 9 is designed at its proximal end 12 such that the latter is used for mounting or coupling the safety cap 18. For this a sleeve wall 47 of the largely cylindrical or tubular activating sleeve 9 in the region of its proximal end 12 has a thinner wall and thus forms a mounting area on the outside of the sleeve wall 47. A cap casing 49 grips over the mounting area 48 on the side facing away from the longitudinal axis 13 and is thus preferably designed to run flat relative to the exterior of the sleeve wall 47.

Furthermore, the activating sleeve 9 at its proximal end 12 in the region of the longitudinal axis 13 has at least one wedge-shaped activating element 50. Said activating element 50 can be designed to be continuous over the circumference and on the side facing the drive unit 4 has a conical surface 51 tapering to the side averted from the drive unit 4. After removing the safety cap 18 with its safety pin 19 upon a relative displacement of the activating sleeve 9 relative to the support housing 2 it is possible to displace the ends of the holding arms 16 on either side of the conical surface 51 radially inwards—i.e. in the direction of the longitudinal axis 13, and in this way release the holding disc 17. This release process is usual with such injection devices 1 and is thus generally known in specialist circles. Therefore, a description of the detailed design of this activating or triggering mechanism for the first drive unit 4 is not given here.

As already described above, FIG. 3 shows the sterilised storage position of the injection device 1, in which the front holding chamber 29 and the cannula 20 coming later into connection or contact with the patient 10 for the injection and the associated administration of the medicine 14 is in a completely sterilised state. Furthermore, in the region of the proximal end 12 of the injection device 1 a detent device 52 is shown in a simplified form, which causes a locking effect between the support housing 2, in particular the rear support housing part 28 and the activating sleeve 9.

Thus the rear support housing part 28 has on its external surface and in the region of the proximal end 12 at least two detent noses 53, 54 spaced apart from one another in the direction of the longitudinal axis 13, which cooperate with a detent element 55 arranged on the activating sleeve 9 in two different longitudinal positions. The detent element 55 formed on the activating sleeve 9 is preferably a component of the sleeve wall 47 and can for example be connected to a resilient detent arm or formed by the latter. The first detent nose 53 is thus arranged closer to the proximal end 12 than the other detent nose 54. The spacing of the two detent noses 53, 54 corresponds preferably to the triggering movement of the activating sleeve 9 relative to the support housing 2, which is necessary to release at least the first drive unit 4 and thus activate the injection procedure. The two detent noses 53, 54 define the relative positions of the support housing 2 with respect to the activating sleeve 9 on the one hand in the storage position and on the other hand in the injection position. Thus only a relative longitudinal displacement of the activating sleeve 9 with respect to the support housing 2 is possible from the storage position to the injection position, but a relative longitudinal adjustment in the opposite position is reliably prevented.

The activation or triggering of the injection device 1 for the injection process from the storage position to the injection position is performed in that the entire injection device 1 is held by the hand of a user on the activating sleeve 9 and then the safety cap 18 is removed from the proximal end 12 of the activating sleeve 9. Thus the injection device 1 is activated for triggering and the following injection process. Subsequently, the entire injection device 1 with its distal end 11 is positioned on the point of the patient 10 where the medicine 14 is to be administered. In this way, the distal end of the needle protection element 7 and if necessary the sealing stopper 36 arranged on the front support housing part 27 in the opening 35 is supported thereon. By displacing the activating sleeve 9 in the direction of the distal end 11 and thus towards the patient 10, by the support of the support housing 2 on the body part of the patient 10, there is a relative displacement of the activating sleeve 9 in relation to the support housing 2. In this way, as already described above, the first drive unit 4, in particular the locked holding arms 16, is displaced by the activating element 50 radially inwards and in this way the locking with the holding disc 17 is released.

The relative axial displacement movement causes the resilient detent element 55 to disengage from the first detent nose 53, slide over the second detent nose 54 and afterwards support itself on this second detent nose 54. In this way the support housing 2 is held fixed in position relative to the activating sleeve 9. This locking is achieved in both axial directions, whereby the first support is performed between the holding arms 16 and the activating element 50 and the second support between the second detent nose 54 and the detent element 55.

Furthermore, the activating sleeve 9 in the region of the distal end 11 and on its internal surface 56 has a stop surface 57, which is preferably aligned perpendicular to the longitudinal axis 13. Said stop surface 57 can preferably be designed or arranged continuously over the inner circumference of the activating sleeve 9 and is preferably formed by a cylindrical or tubular recess in the sleeve wall 47.

Also the needle protection element 7 is secured under pretensioning of the second drive unit 8 relative to the support housing 2, in particular the front support housing part 27 in the storage position. This relative and detachable securing can best be seen in FIGS. 2 and 3 in the region of the distal end 11. The support housing 2 or the front support housing part 27 has at its distal end 11 on its external surface 58 a preferably continuous stop element 59. On the needle protection element 7 corresponding thereto at least one rocker-like lever element 60 is provided, which in the direction of the longitudinal axis 13 comprises spaced apart lever ends 61, 62. The lever end 61 lying closer to the distal end 11 is supported in the storage position of the injection device 1 on the previously described stop element 59 of the front support housing part 27 of the support housing 2. The additional lever end 62 projects into the recess of the activating sleeve 9 described above and in the direction of the stop surface 57. Depending on the selected spacing between the lever end 63 and the stop surface 57 the triggering time described in more detail below for the needle protection element 7 or the second drive unit 8 cooperating therewith can be varied. The second drive unit 8 with its resilient driving means 40 is supported in the region of its end section facing the proximal end 12 on the backspringing wall part 38. Furthermore, the second drive unit 8, in particular the driving means 40, is supported by its end section facing the distal end 11 on a face side of the needle protection element 7 facing the proximal end 12. In this way the driving means 40 of the second drive unit 8 is arranged on the one hand, as viewed in radial direction, between the support housing 2 and the activating sleeve 9 and on the other hand, as viewed in axial direction, on the backspringing wall part 38 of the support housing 2 and the face side of the needle protection element 7. By means of the support on the face side of the needle protection element 7 the driving means 40 of the second drive unit 8, as viewed in axial direction, is arranged behind the needle protection element 7 and thus on the side facing the proximal end 12 or the end section formed there. In this way on the needle protection element 7 it generates a pressing force directed towards the distal end 11. This pressing force is transferred from the needle protection element 7 via the lever element 60 arranged or formed thereon to the stop element 59 arranged on the support housing 2 and is thus supported there.

As already described above, the entire needle arrangement 6, in particular the cannula 20 is arranged with its needle end 22 facing the cartridge seal 26 spaced apart from the latter in the storage position. Furthermore, the needle support 23 is held axially displaceably in the guiding element 24 or mounted therein, whereby in the storage position the needle support 23 is secured by at least one detachable holding element 63 relative to the guiding element 24. This can best be seen from the view of FIG. 1.

Figure 2:
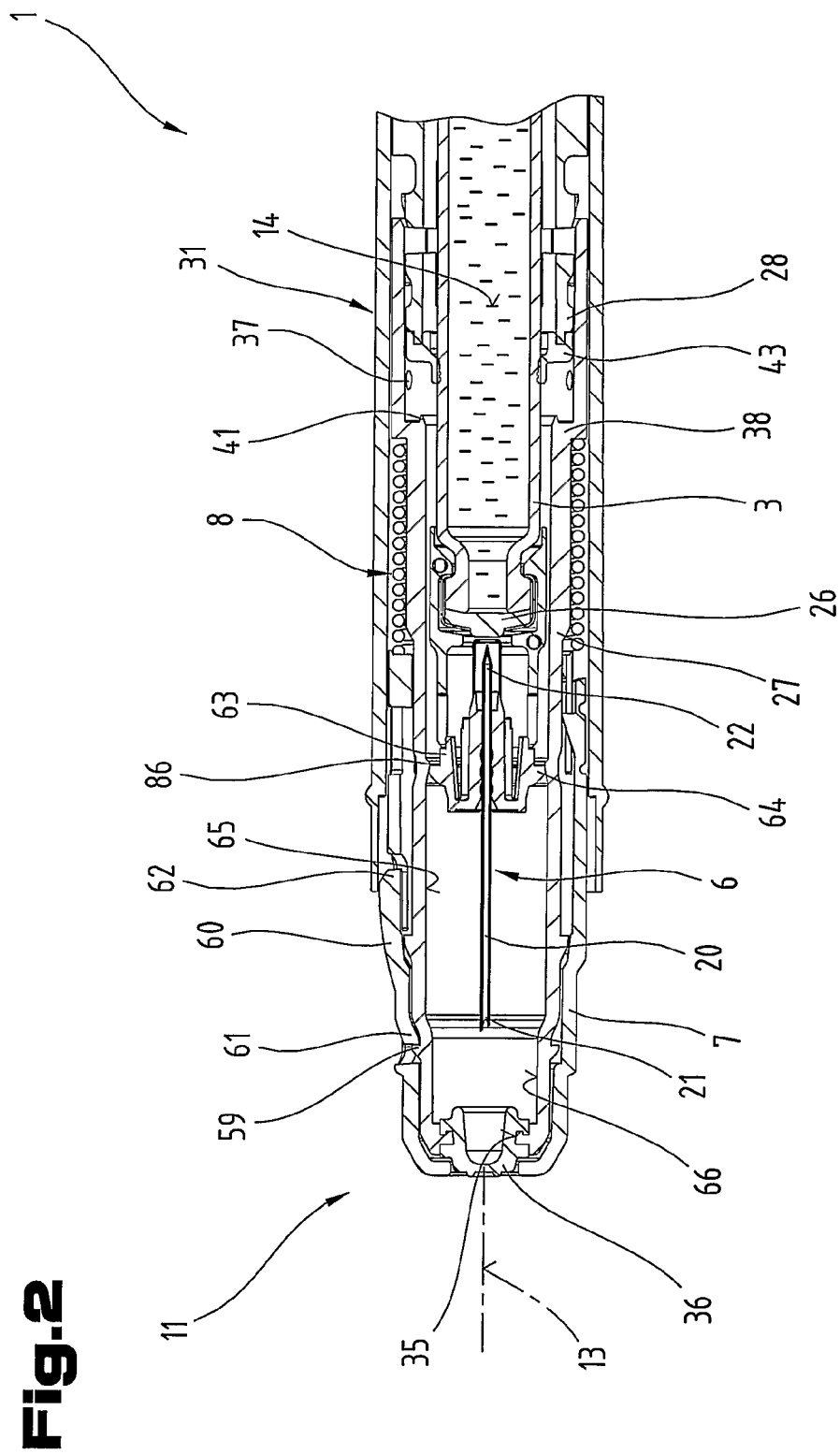
FIG. 2 shows a partial section of the injection device according to FIG. 1, but in a different cross sectional plane.

As can be seen better from FIGS. 2 and 3 an adjusting cam 64 is allocated to the holding element 63 of the needle support 23 or arranged thereon, which adjusting cam projects over the needle support 23 on the side averted from the longitudinal axis 13. The front support housing part 27 of the support housing 2 in this section has an internal clear dimension or a cross section which is designed to be approximately cylindrical and thereby the adjusting cam 64 is arranged immediately adjacent thereto until bearing lightly against an inner wall 65 of the sleeve-like support housing part 27. If now by means of the first drive unit 4 the cartridge 3 together with needle arrangement 6 is moved in the direction of the distal end 11, firstly the needle end 21 facing the distal end 11 sticks through the sealing stopper 36 arranged in the opening 35 of the front support housing part 27 and then enters directly into the surface section of the patient 10 provided for the administration.

Figure 4:
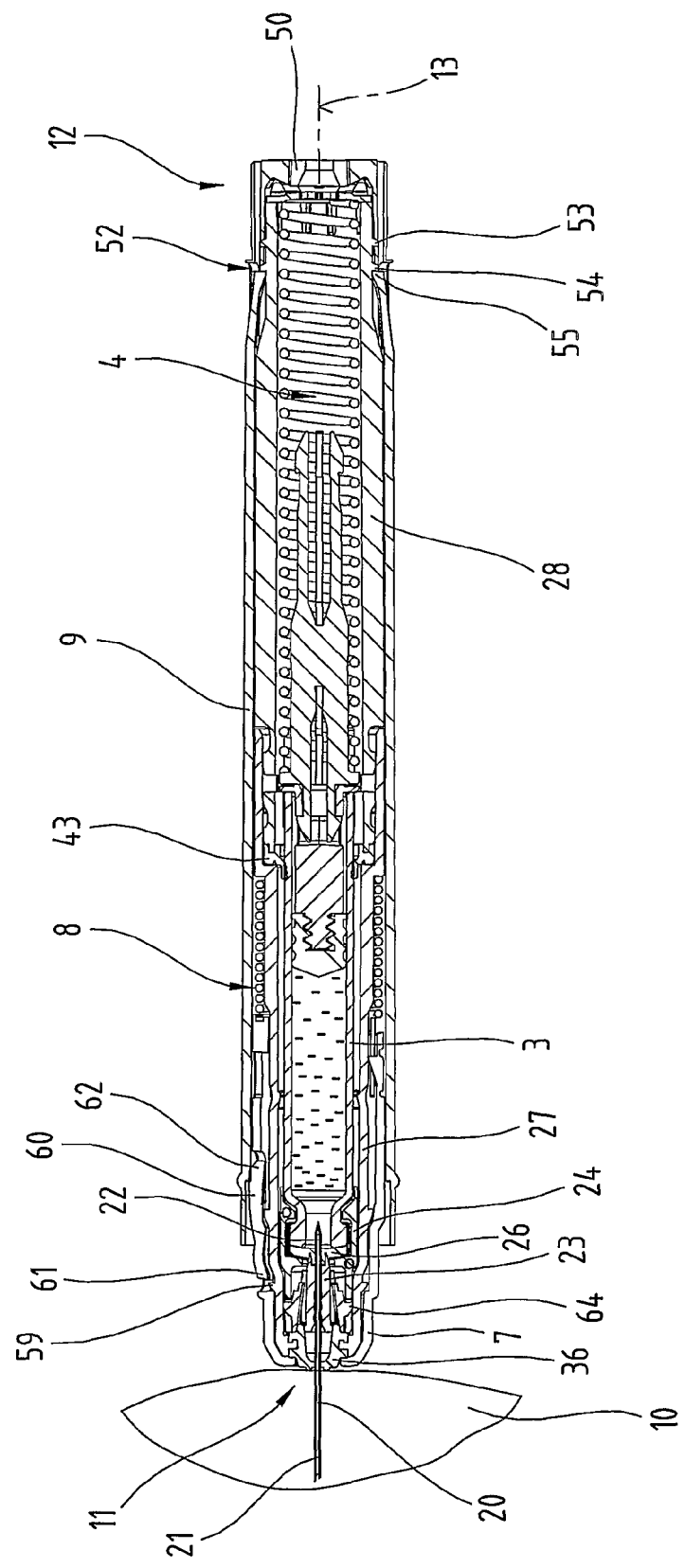
FIG. 4 shows the injection device according to FIGS. 1 to 3, during the administration procedure of the medicine, in axial cross section and simplified representation.

The activated and inserted position of the cannula 20 into the patient 10 can best be seen from FIG. 4. In this case the cartridge 3 together with the needle arrangement 6 has been shifted in the direction of the distal end 11. Furthermore, in the region of the distal end 11 on the internal wall 65 of the front support housing part 27 a control cam 66 projecting in the direction of the longitudinal axis 13 is formed, which for example is formed by a narrowing of the wall part forming the front support housing part 27. Likewise the formation of a rib or web on the internal wall 65 would be possible. The control cam 66, which is offset in the direction of the longitudinal axis 13, with the associated reduction or narrowing in the cross section, comes into engagement with the adjusting cam 64 during the displacement movement of the needle arrangement 6, and is shifted together with the holding element 63 radially inwards in the direction of the longitudinal axis 13. By means of this displacement the holding element 63 is disconnected from the guiding element 24. Because of this release and the mechanical bearing of the needle support 23 on the sealing stopper 36 arranged at the distal end 11, there is a further relative displacement between the needle support 23 and the guiding element 24. By means of this relative displacement the needle end 22 facing the proximal end 12 penetrates the cartridge seal 26, whereby a flow connection is now created between the inner chamber of the cartridge 3 via the cannula 20 to the insertion point into the patient 10. By means of the mechanical stop of the needle support 23 against the sealing stopper 36 and the completion of the relative displacement between the needle support 23 and the guiding element 24, also the cartridge 3 is secured fixed to the support housing 2. The sealing stopper 36 is thus designed at the end facing the needle support 23 or the guiding element 24, such that the latter also performs a damping function for completing the adjusting movement and cartridge 3 mostly made of glass does not get broken by the sudden displacement movement and the associated impact at the distal end 11. Therefore, a preferably circumferential flange projects from the opening 35 in the direction of the front holding chamber 29, which thereby comes into contact with the needle arrangement 6.

By means of the further pressure effect or force loading of the drive unit 4 in the direction of the distal end 11 a cartridge stopper 68 arranged on a piston rod 67 is pushed into the inner chamber of the cartridge 3 and thus injects the medicine 14 via the cannula 20 injected at this time into the patient 10.

During the relative displacement of the activating sleeve 9 relative to the support housing 2 and the associated triggering of the first drive unit 4 the second lever end 62 of the lever element 60 facing the proximal end 12 comes into contact with the stop surface 57 formed on the internal surface 56 of the activating sleeve 9. In this way the lever end 62 facing the proximal end 12 is pivoted radially in the direction of the longitudinal axis 13. Then the rocker-like mounting of the lever element 60 causes the first lever end 61 of the lever element 60 facing the distal end 11 to disengage from the stop element 59 by a radial pivoting to the side averted from the longitudinal axis 13. Thus the support of the needle protection element 7 on the support housing 2, in particular the front support housing part 27, is released, and simultaneously the second drive unit 8 is activated. In this way, after the completion of the injection procedure and the removal of the injection device 1 from the patient 10 immediately the needle protection element 7 with the drive unit 8 cooperating therewith is shifted from its non-effective position into the position covering the needle end projecting after the injection procedure over the distal end of the support housing 2. It is advantageous, if with the axial displacement of the activating sleeve 9 relative to the support housing 2 the release of both the first and second drive units 4, 8 is performed simultaneously.

FIG. 5 shows the protected position of the cannula 20 after the injection procedure and the removal from the injection site on the patient inside the needle protection element 7.

In order to prevent the unintentional restoring of the needle protection element 7 from the protecting and covering position to a new release position of the needle end 21, the needle protection element 7 also has at its proximal end 12 at least one elastically deformable safety element 69, which can be designed as an elastically deformable lever. The needle protection element 7 is shifted during its relative displacement relative to the support housing 2 into the position covering the needle arrangement 6 by the drive unit 8. The restoring of the needle protection element 7 in the direction of the proximal end 12 is prevented by the support of the safety element 69 on the stop surface 57 formed on the internal surface 56 of the activating sleeve 9. In this case the needle protection element 7 is displaced by means of the second drive unit 8 via a predefined displacement movement up to a mechanical stop. The safety element 69 thus projects in this case into the free space in front of the stop surface 57. Furthermore, the safety element 60 can be arranged at a specific distance in front of the stop surface 57 or also immediately adjacent thereto. The locking position of the safety element 60 is additionally supported or secured in the position of the needle protection element 7 covering the needle arrangement 6 by an adjusting element 70 arranged on the support housing 2. The adjusting element 70 can be designed as a circumferential web-like shoulder on the support housing 2 or the front support housing part 27, whereby the adjusting element 70 during the relative displacement of the needle protection element 7 pushes or moves the safety element 69 radially to the side averted from the longitudinal axis 13 relative to the support housing 2. By means of this mechanical locking of the safety element 69 onto the stop surface 57 and the radial pretensioning by the adjusting element 70 a secured covering of the cannula 20 by the needle protection element 7 is ensured.

The axial adjustment movement of the needle protection element 7 relative to the support housing 2 can be ended by a positive stop between a detent element 71 arranged on the proximal end 12 and the adjusting element 70 arranged on the support housing 2 in the direction of the distal end 11. In this way the needle protection element 7 is adjusted by a predefined adjustment movement in the direction of the distal end 11, whereby in this position the cannula 20 of the needle arrangement 6 is completely covered. This can best be taken from FIG. 6.

Furthermore, it can also be taken from FIG. 5 that the needle support 23 on its side facing the cartridge seal 26 comprises a sealing shoulder 85 which completely surrounds the cannula 20 at a predeterminable radial distance and projects in axial direction. This shoulder is designed, as viewed in axial cross section, to taper wedge-like in the direction of the cartridge seal 26. On penetrating the cartridge seal 26 with the cannula 20 there may be leakages in the immediate penetration area between the cannula 20 and the cartridge seal 26. The seal is then produced by the sealing shoulder 85 in cooperation with the elastically deformable cartridge seal 26, as the sealing shoulder 85 penetrates into the material and also pushes the latter against cannula 20.

FIG. 7 shows the holding disc 17 of the safety device 5 in a plan view and in a simplified representation. Thus the holding disc 17 in its centre has a preferably round opening 72 as well as recesses 73 adjoining the latter and extending radially outwards. Independently of this it would also be possible to make the cross section of the throughput 72 polygonal, in particular quadratic, as indicated by dashed lines. The number of recesses 73 thus corresponds to the number of holding arms 16 of the first drive unit 4 to be secured in the storage position. In the present exemplary embodiment four holding arms 16 are provided evenly distributed over the circumference, whereby for better positioning, guiding and mounting of the holding arms 16 in the holding disc 17 recesses 73 are provided. Furthermore, the holding disc 17 on its external circumference has additional segment-like shoulders 74. Said shoulders 74 are used for connecting the holding disc 17 to the rear support housing part 28 of the support housing 2. This can be for example in the form of a snap or detent connection.

The administration of the medicine 14 supplied in the cartridge 3 can be performed in the following manner. The two drive units 4, 8 are held secured in their pretensioned position inside the injection device 1, whereby the front holding chamber 29 together with the entire needle arrangement 6 is in a sterile state. If the injection is now to be administered, firstly by removing the safety device 5, i.e. the safety cap 18 together with the safety pin 19, the first drive unit 4 is released for its triggering or activation. The user holds the entire injection device 1 on the activating sleeve 9 and places the latter with its distal end 11 on the body part of the patient 10 to receive the medicine 14. In this way the support of the support housing 2 together with the needle protection element 7 arranged thereon on the surface of the patient 10 is achieved.

By means of the axial adjustment movement of the activating sleeve 9 in the direction of the distal end 11, the first drive unit 4 is triggered or activated, whereby the cartridge 3 together with the needle arrangement 6 is adjusted automatically in the direction of the distal end 11. During this axial adjustment movement additionally the needle support 23 together with the cannula 20 is released from the locked first position on the guiding element 24 and the needle end 22 is penetrated through the cartridge seal 26. Prior to this penetration the needle end 21 facing the distal end 11 has already been pushed into the patient 10, whereby the flow connection between the needle end 22 averted therefrom with the internal chamber of the cartridge 3 is performed immediately afterwards. Immediately afterwards or also simultaneously with the axial displacement of the activating sleeve 9 also the second drive unit 8 is triggered for the movement of the needle protection element 7. By means of the first drive unit 4 the medicine 14 is the administered to the patient 10. After completing the administration the entire injection device 1 is removed from the patient 10. By means of the already activated or triggered second drive unit 8 during the removal of the injection device 1 from the patient 10 the needle protection element 7 is adjusted until the cannula 20 is mounted completely therein or the detent part 71 of the needle protection element 7 comes to bear against the adjusting element 70. At the same time as the complete axial displacement of the needle protection element 7 into the covering position the latter is hindered by means of the safety element 69 by supporting on the stop surface 57 against a repeat restoring into a release position of the needle end 21.

FIGS. 8 to 10 show a further and if necessary independent embodiment of a holding shell 75 for holding the injection device 1 or a plurality of the latter are shown, whereby in turn for the same parts the same reference numbers or component names are used as in the previous FIGS. 1 to 7. In order to avoid unnecessary repetition reference is made to the detailed description in the preceding FIGS. 1 to 7.

The holding shell 75 shown here can represent in itself an independent solution according to the invention. In this case the objective of the invention can be seen to create a holding shell 75, which is used for holding preferably several injection devices 1 arranged next to one another and in which also the sterilisation of the injection device 1 can be performed, whereby after the sterilisation the subsequent sealing process and the associated sterile sealing of the sterilised space inside the injection device 1 can also be performed simultaneously with the injection device 1 located in the holding shell 75.

The holding shell 75 can in this case also be denoted as a tray, which is formed for example from a deep-drawn foil from a heat-deformable material, such as for example a plastic. The injection device 1 shown in FIGS. 8 and 9 in the holding shell 75 is uncut and only represented in a simplified form.

The holding shell 75 is designed to be bath-shaped and comprises a base 76 and side walls 77 projecting upwards from the latter. On the side of the side walls 77 facing away from the base 76 the holding shell 75 has a container edge 78. The latter is preferably designed to be flange-like projecting outwards and is used in order to be sealed by a cover 79 shown in simplified form in FIG. 8. The cover 79 covers the entire inner chamber provided for holding the injection device 1 and delimited by the holding shell 75 and can be selected from the material or substance described above, as described for covering the injection device 1. As the paper-fleece-like fibrous material from the thermally welded fibres allows a sealing or welding process with the basic material of holding shell 75 with a suitable selection, in the region of the container edge 78 the cover 79 can be sealed continuously all around in this manner. It would also be possible however to secure the cover 79 with a sealed adhesive connection or the like on the container edge 78 of the holding shell 75. It is essential with the material of the cover 79 that it is possible to perform the gassing and the associated sterilisation through the cover 79 without subsequently germs and bacteria passing through the cover 79. The material of the holding shell 75 is then selected so that here likewise a completely germ and bacteria-tight seal is achieved.

Depending on the external dimensions of the activating sleeve 9, in the region of the base 76 holding elements 80 are formed here in rows arranged behind one another in the region of the base 76. The latter are used for clamping the injection device 1 and thus determine the position of the injection devices 1 inside the holding shell 75. It would also be possible however to dispense with the clamping action of the holding elements 80 and to omit this completely. Independently of this it would also be possible instead of the clamping effect of the holding elements 80 between the injection devices 1 arranged in the holding shell 75 to simply have separating webs in order to achieve at least a rough positioning or mutual positioning of the injection devices 1 relative to one another.

Furthermore, from an overview of the FIGS. 8 to 10 in the region of the distal or proximal end 11, 12 of the injection device it can be seen that on the opposite side walls 77 deformable wall sections 81 are arranged or formed respectively. Said individual wall sections 81 are thus immediately adjacently allocated to the distal end 11 or proximal end 12. In the coupling position of the two support housing parts 27 and 28, in which access is possible via the throughput 37 into the front holding chamber 29, support sections 82 of the deformable wall sections 81 aligned preferably at right angles to the base 76 project directly up to the distal or proximal end 11, 12. With a corresponding selection of dimensions here a sufficient axial alignment of the individual injection devices 1 is achieved inside the holding shell 75. It would however be possible independently of this to dispense with the shapeable wall sections 81 and to form the support section or sections 82 directly by the side walls 77 in a virtually planar design. In this case it is possible to ensure the deformation movement of the side walls 77 to perform the previously described adjustment movement of the two support housing parts 27, 28 relative to one another.

Afterwards on said support section 82 the deformable wall section 81 comprises step-like outwards expanding and semi-circular deformation sections 83. The step-like deformation sections 83 arranged behind one another thus subsequently form a seal with the support section 82 in the direction of the container edge 87. The beginning of the semi-circular deformation sections 83 is thus approximately at the level of the longitudinal axis 13 of the injection device 1 in a position clamped in the holding shell 75 and preferably parallel to the base 76 or the container edge 78. By means of the step-like or step-shaped arrangement behind one another a very large deformation movement of the wall sections 81 is achieved, without these deformation movements damaging the holding shells 75. This is essential as otherwise it would be possible for germs or bacteria to enter the otherwise completely sealed holding chamber of the holding shell 75.

FIG. 8 shows in a simplified manner with arrows marked "F" aligned towards one another, that by applying the indicated pressure force the aforementioned adjustment movement can be performed between the two support housing parts 27, 28.

It is also shown in a simplified form in FIG. 8 that the injection device 1 can have a marking 84, which can be seen in the first coupling position of the two support housing parts 27, 28, but cannot be identified or seen in the second coupling position shown in FIG. 9. Apart from this other options would also be possible to make the correct closure of the front holding chamber 29 visually identifiable without requiring complicated monitoring devices. This would be possible for example by a simple red/green marking in a viewing window in the activating sleeve 9, whereby for example the red marking can show the first coupling position and the green marking the second sterile coupling position between the two support housing parts 27, 28. This can be performed by the position of the front support housing part 27 relative to the activating sleeve 9, whereby the shown marking is dependent on the respective position.

By means of the additional shaping or use of the holding shell 75, it is possible to provide the injection device 1 in a premounted state for sterilisation, in order to perform this for example at a further location provided for this, and after the sterilisation is complete to adjust the two support housing parts 27, 28 into the second coupling position. By means of the complete enclosure of the injection devices 1 inside the holding shell 75 and the thus associated covering 79 also non-sterile transport movements after sterilisation up to the complete sealing in the second coupling position can be planned.

After the sterilisation has been carried out thus all of the components of the injection device 1 accessible by the ETO gassing are sterilised or the latter have such a state. The subsequent adjustment of the two support housing parts 27, 28 relative to one another are performed opposite one another and the associated completely sealed closure of the front holding chamber 29 can then be performed by means of separate mechanical device, not show in more detail here. The correct sealing can be performed by the previously described visual or sensory control of the marking 84.

After pushing together the two support housing parts 27, 28 the cover 79 can be removed from the holding shell 75, and the sterilised injection devices 1 removed from the holding shell 75 and if necessary further packed into individual packaging.

Figure 11:
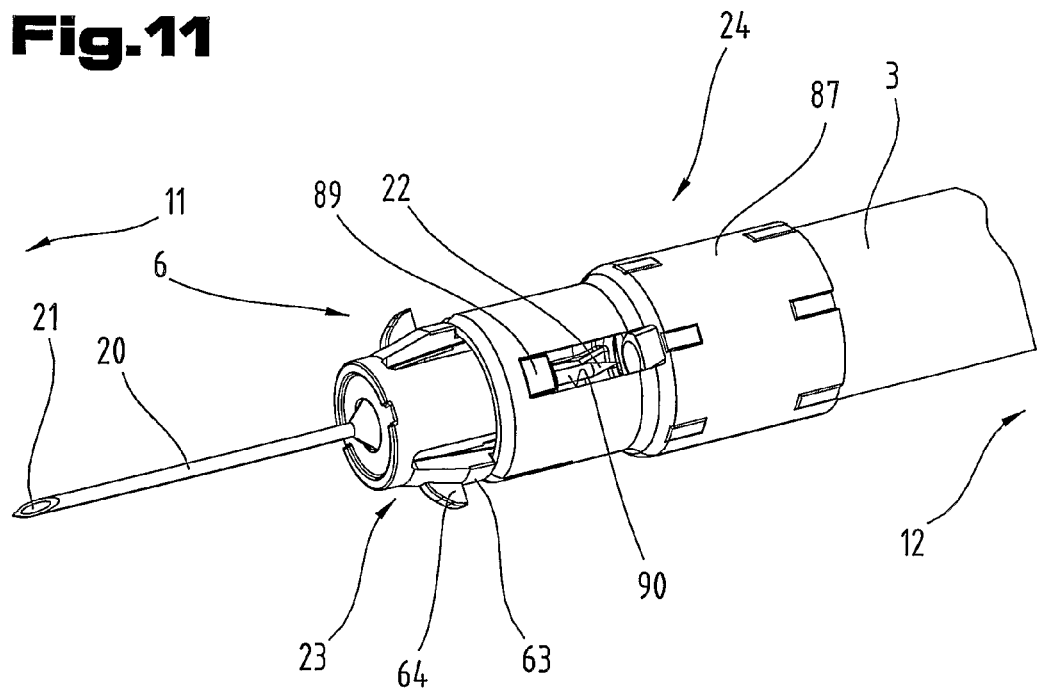
FIG. 11 shows the needle arrangement in the coupled position on the cartridge according to FIGS. 1 to 6, in a simplified view.
Figure 12:
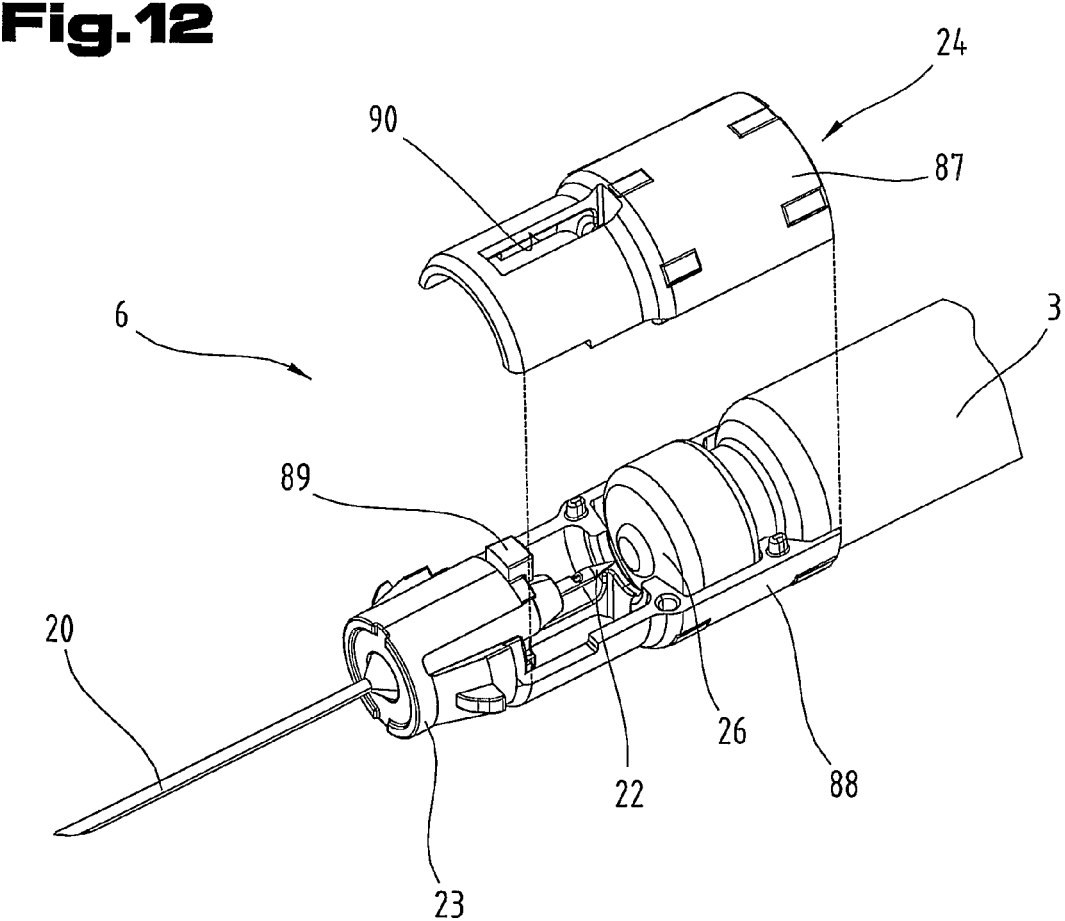
FIG. 12 shows the needle arrangement according to FIG. 11 with a raised guiding element of the guide element, in a simplified view.

In FIGS. 11 and 12 a further and if necessary independent embodiment of the needle arrangement 6, in particular the needle holder 23 and the guiding element 24, of the injection device 1 is shown, whereby again for the same parts the same reference numbers and component names are used as in the preceding FIGS. 1 to 7. To avoid unnecessary repetition, reference is made to the detailed description in the preceding FIGS. 1 to 7.

As already described above, the needle support 23 and the cannula 20 mounted and held therein is mounted jointly in the guiding element in axial direction displaceable lengthways relative to said guiding element 24. FIG. 11 also shows the support of the holding element 63 on the guiding element 24. On the holding element 63 the previously described adjusting cam 64 is arranged, which on the axial displacement of the cartridge 3 together with the guiding element 24 and the needle support 23 releases the lock and thus the injection process of the needle end 22 into the cartridge seal 26 is performed.

The guiding element 24 is formed in this embodiment shown here from two guiding elements 87, 88, which can be joined together like half-shells to form the tubular guiding element 24.

By means of the raised position shown in FIG. 12 of the guiding part 87 lying at the top here the spaced apart position of the needle end 22 from the cartridge seal 26 can easily be seen. Furthermore, the needle support 23 preferably has diametrically opposite guiding shoulders 89, which engage into a guiding slot 90 in the guiding part 87 and/or 88.

In the mounted position shown in FIG. 11 of the guiding element 24 the needle support 23 is held fixed in both axial directions relative to the guiding element 24. The guiding shoulder(s) 89 delimit in cooperation with the guiding slot 90 the adjustment movement of the needle support 23 in the direction of the distal end 11. The holding element(s) 63 however prevent an axial displacement of the needle support 23 in the direction of the proximal end 12 up to its release by the interaction of the adjusting cam 64 with the control cam 66 of the support housing 2. The relative axial displacement movement of the needle support 23 in the direction of the proximal end 12 and the thus associated penetration of the needle end 22 through the cartridge seal 26 can be delimited by the selected longitudinal extension of the guiding slot 90.

The two guiding elements 87, 88, designed here as half-shell parts, are prevented from falling out in the assembled state by the bearing thereof against the internal surface 45 of the support housing 2 in particular the front support housing part 27. In this way a simple assembly is achieved with a good connection. Furthermore, a mutual locking of the two guiding parts 87, 88 is possible by an offset arrangement of pins and pin mounts.

This axial guiding has the advantage that also an axial injection movement of the cannula 20 relative to the longitudinal axis 13 is performed into the tissue of the patient 10 or user.

Figure 13:
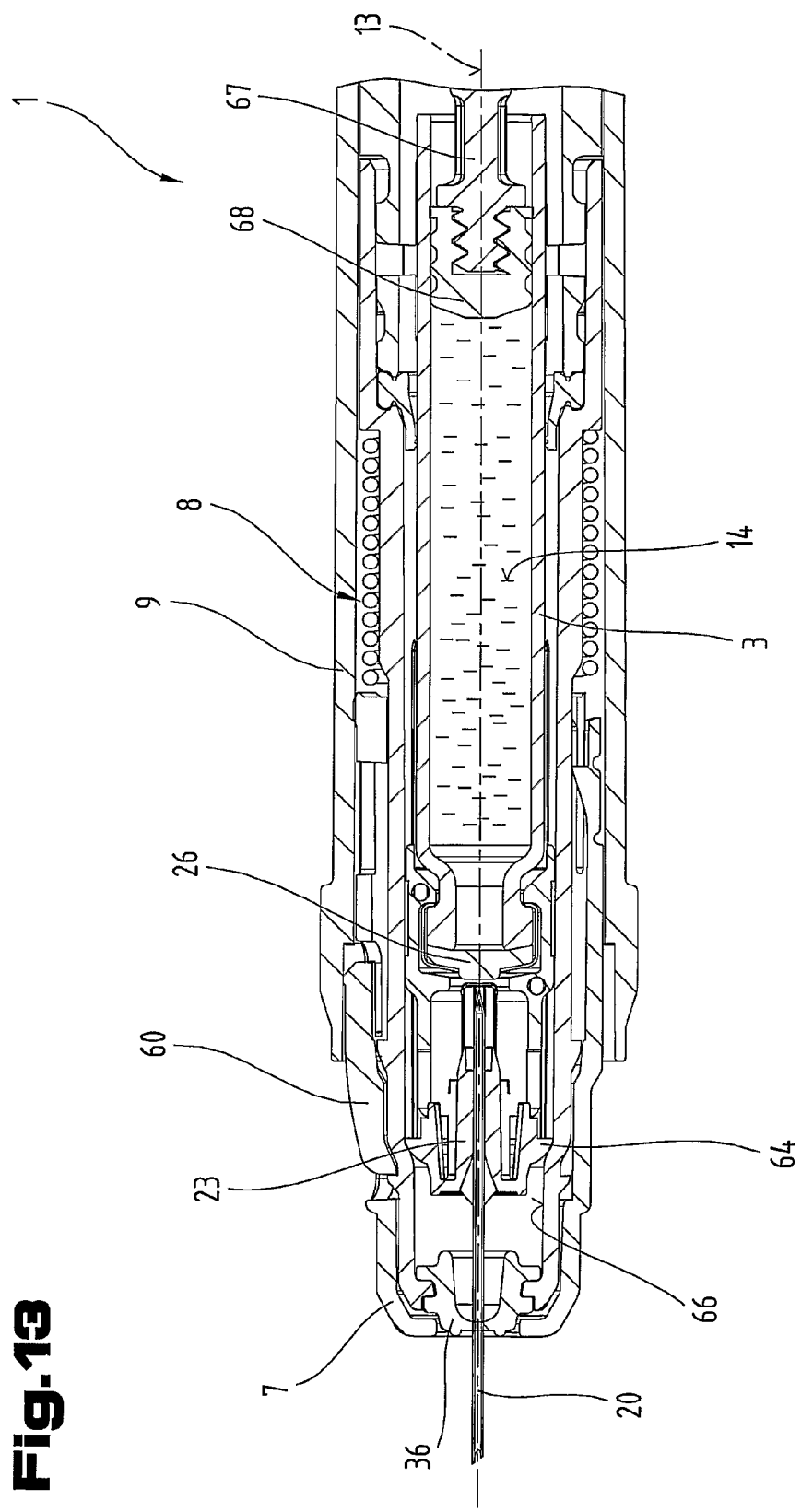
FIG. 13 shows the needle arrangement in the coupled position on the cartridge according to FIGS. 1 to 6 during the adjustment movement for administering the medicine in a position immediately prior to the cooperation of the adjusting cam with the control curve, in axial cross section.

FIG. 13 shows the already described in detail interaction of the control cam 66 of the support housing 2, in the present exemplary embodiment of the front support hosing part 27, with the adjusting cam 64 arranged on the holding element 63 in an enlarged view.

This results in the radial displacement and the associated release of the locking between the holding element 63 and the guiding element 24. Depending on the position of the control cam 66, as viewed in axial direction, also the release for the injection movement of the needle end 22 into the cartridge seal 26 can be determined. The earlier the release takes place the sooner the cartridge 20 is in flow connection with the inner chamber of the cartridge 3 containing the medicine 14.

Figure 14:
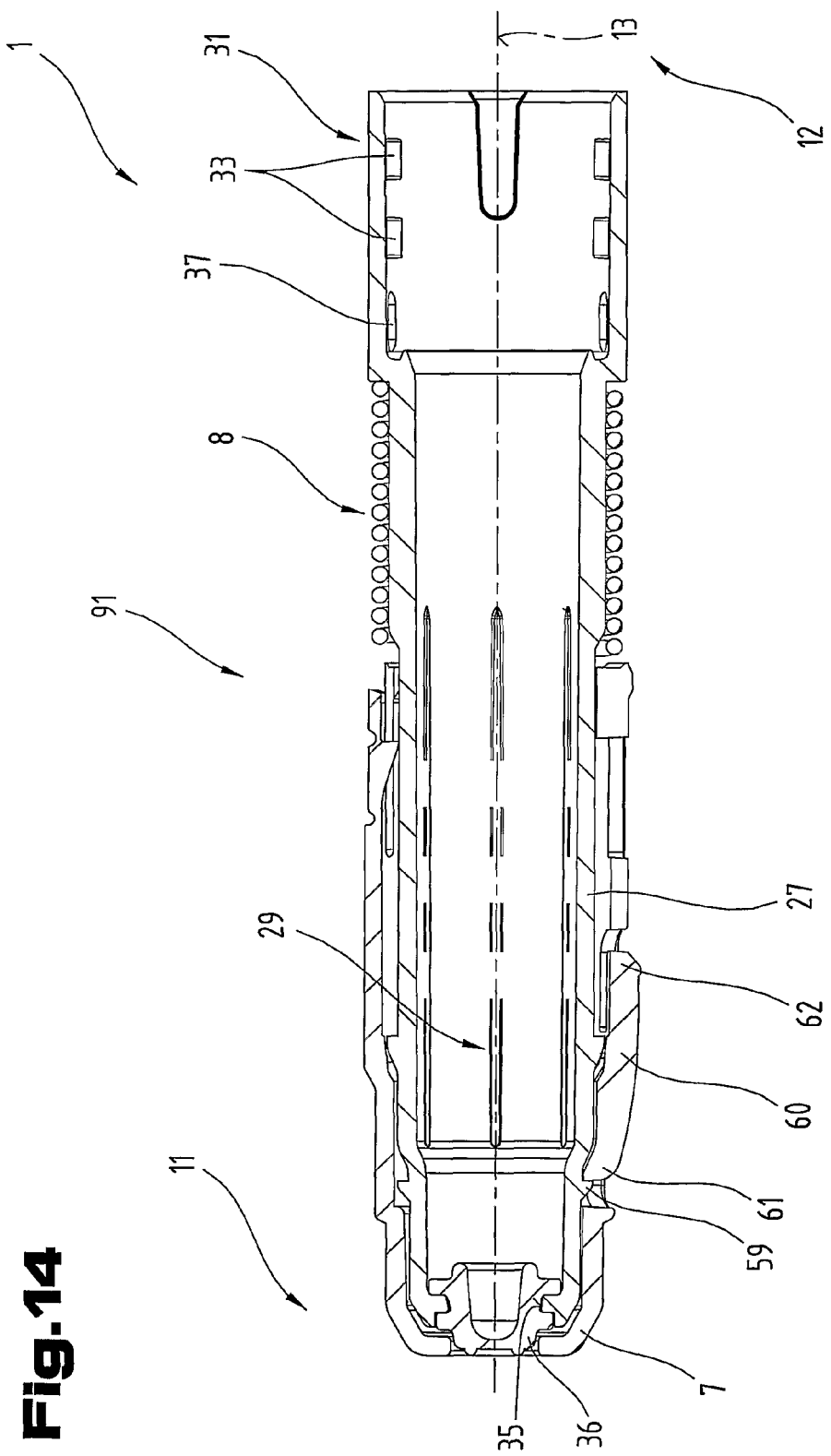
FIG. 14 shows a first premounted component group of the injection device in the region of the front support housing part, in axial cross section.
Figure 15:
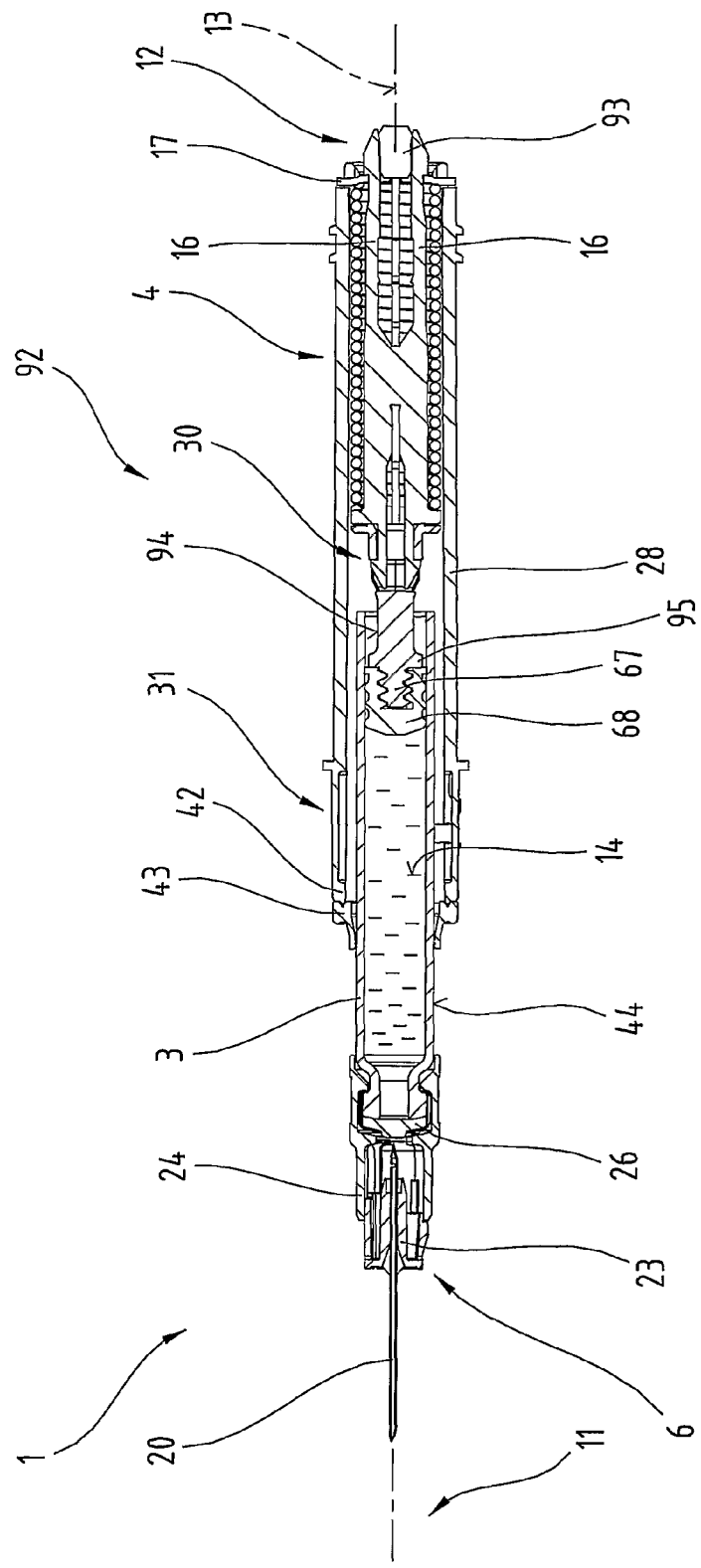
FIG. 15 shows a second premounted component group of the injection device in the region of the rear support housing part, in axial cross section.
Figure 16:
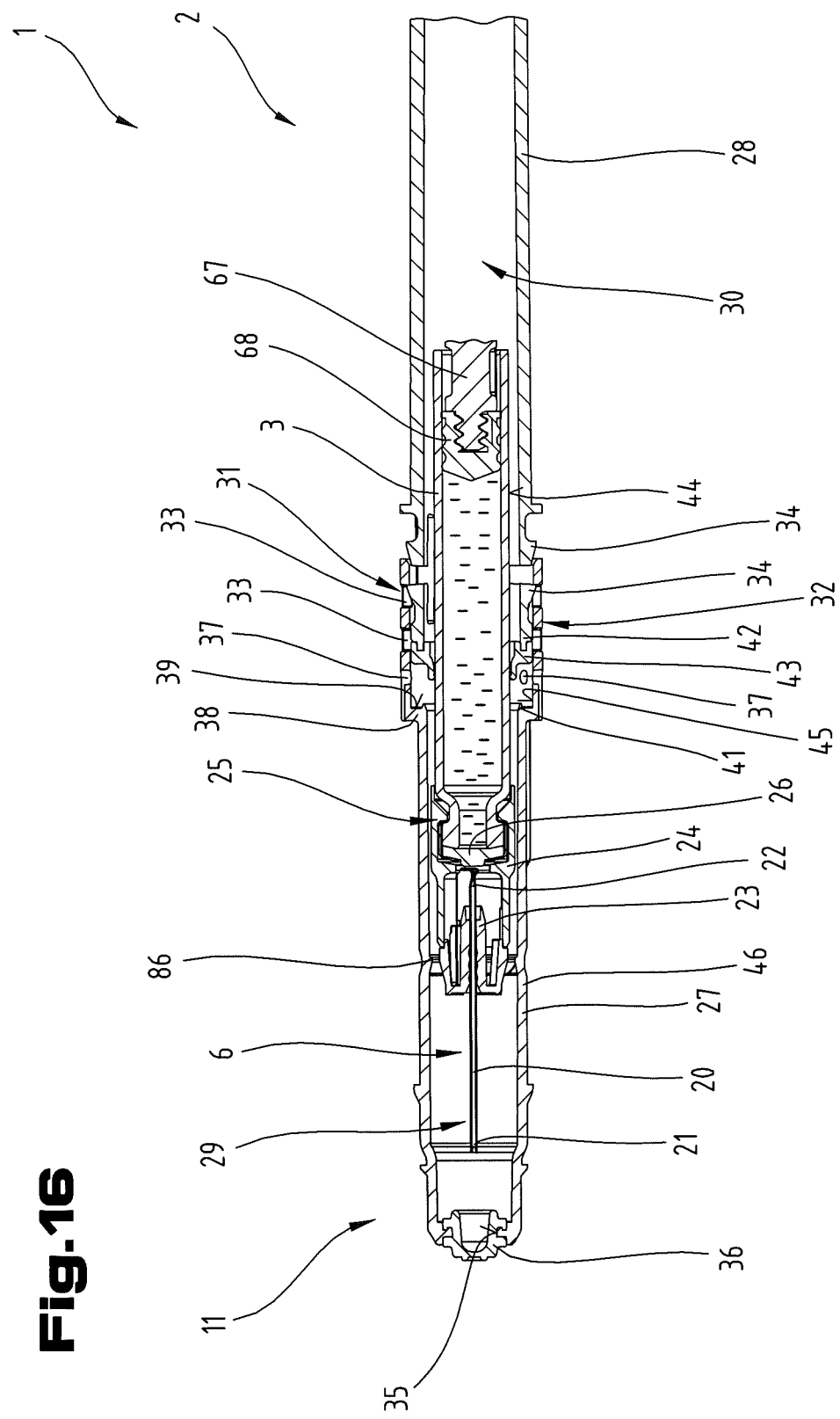
FIG. 16 shows an injection device showing the support housing with the cartridge and the needle arrangement inside the support housing in a first coupling position.

In FIGS. 14 and 15 the injection device 1 according to the view in FIGS. 1 to 7 and 11 to 13 is shown, wherein for the same parts the same reference numbers and component names have been used as in the preceding Figures. To avoid unnecessary repetition reference is made to the detailed description of the preceding FIGS. 1 to 13.

The individual components forming the injection device 1 are designed such that the latter can be assembled or preassembled into component groups or units 91, 92. In a subsequent additional assembly stage then the two component units 91, 92 are joined together with the remaining components, as shown in FIG. 1.

Thus a first component 91 in the region of the distal end 11 of the injection device 1 comprises the front support housing part 27, the sealing stopper 36 and the needle protection element 7 adjustable with the second drive unit 8. The needle protection element 7 is supported and locked in turn by the previously described lever element 60 on the stop element 59 of the front support housing part 27. The second drive unit 8, which is formed here by a spiral compression spring, is supported on the one hand on the step-like connecting section 31 of the front support housing part 27 and on the other hand on a face side of the needle protection element 7 facing the proximal end 12. By means of the pretensioned drive unit 8 according to the already described release of the lever element 60 the axial adjustment of the needle protection element 7 can be performed into the position covering the need or the cartridge 20.

The second component 92 in the region of the proximal end 12 of the injection device 1 comprises in turn the rear support housing part 28, the first drive unit 4 mounted therein, the cartridge 3 with its cartridge stopper 26, the needle arrangement 6, the sealing element 43, the piston rod 67 with the cartridge stopper 68 and the holding arms 16, which can be held in position by means of the holding disc 17. In order to prevent the unintentional release of the first drive unit 4 by means of the disengagement of the holding arms 16 with the holding disc 17, it is shown a simplified manner in FIG. 15, that the holding arms 16 are held by a safety element 93 arranged in the region of the longitudinal axis 13 radially on the side facing away from the longitudinal axis 13. The safety element 93 is preferably designed to be pin-like and is left so long on the component 92 until the final assembly with the component 91 and the activating sleeve 11 and the safety device 5 is performed.

In this way a high degree of prefabrication is achieved, whereby according to the desired medicine also the cartridge 3 can be connected to the needle arrangement 6 arranged thereon via the cartridge stopper 68 to the piston rod 67. The assembly of the cartridge 3 on the piston rod 67 can be performed as a function of the storage ability of the medicine 14.

In this way a simple method for assembling the injection device 1 can be created, in which firstly the previously described components 91, 92 are assembled together with all their individual part and thus form a semi-finished product or intermediate product. In this way also there can be an external manufacture of the individual components and for example the preassembled components 91, 92 can be produced and assembled by different manufacturers. If during the assembly the first component 91 is joined to the second component 92 in the region of the connecting section 31 according to the position shown in FIG. 1, then said component group consisting of the two components 91, 92 is inserted into the activating sleeve 9. Prior to this or also after this then the preferably pin-like safety element 93 in the region of the holding arms 16 is removed and replaced by the cap-like safety device 5 with the safety pin 19. After this the previously described sterilisation can be performed in the inner chamber of the support housing 2, in particular in the region of the needle arrangement 6.

As already shown in FIGS. 1 to 6, the piston rod 67 comprises a radial depression 94, which in the premounted position of the piston rod 67 on the cartridge 3 comes to bear or is arranged on the end of the cartridge 3 facing the proximal end 12. This reduction of the outer dimension, in particular the diameter of the piston rod 67 is performed in order over the entire storage period of the injection device with a possible pivoting of the cartridge 3 relative to the piston rod 67 to prevent damage to the cartridge 3 made mostly or preferably of glass at its proximal end. Thus the piston rod 67 is connected to the cartridge stopper 68. This can be performed preferably by a threaded arrangement. In the immediate bearing area of the piston rod 67 on the cartridge stopper the latter comprises a preferably flange-like shoulder 95. Said shoulder 95 is used for the mutual axial securing between the piston rod 67 and the cartridge stopper 68. The free position designed as a depression 94 of the piston rod 67 thus protects against damage during transport or in the case of unintentionally dropping the entire injection device 1. A further damping support of the cartridge 3 can be performed by the sealing element 43 on the rear support housing par 28, as already described above.

The exemplary embodiments show possible embodiment variants of the injection device 1, whereby it is noted at this point that the invention is not restricted to the specifically shown embodiments thereof, but rather also various combinations of the individual embodiments are possible and this variability due to the teaching on technical proceedings of the present invention lies within the ability of a person skilled in this technical field. Also all conceivable embodiment variants are covered by the scope of protection, which are possible by the combination of individual details of the embodiment variants shown and described.

For form's sake it is mentioned that for a better understanding of the structure of the injection device 1 the latter and its components have been shown partly untrue to scale and/or enlarged and/or reduced in size.

The underlying objective of the independent solutions according to the invention can be taken from the description.

Mainly, the individual embodiments shown in FIGS. 1 to 6; 7; 8 to 10; 11, 12; 13; 14; 15 can form respectively the subject matter of independent solutions according to the invention. The objectives according to the invention and solutions can be taken from the detailed descriptions of said figures.

The invention claimed is:

1. An injection device configured to be adjustable from a storage position to an injection position, comprising:
    a support housing having a distal end to be applied to a patient and a proximal end opposite the distal end, between which a longitudinal axis extends, the support housing further including:
        a front support housing part including a casing, the front support housing part defining an opening at a distal end of the front support housing part and defining a front holding chamber, the casing extending from the opening to a connecting section, and
        a rear support housing part defining a rear chamber, the front support housing part and the rear support housing part adapted to be coupled together in the connecting section via a coupling device in the direction of the longitudinal axis in two different longitudinal positions in a first and a second coupling position;
    an activating sleeve at least partially surrounding the support housing and configured to be adjusted in an axial direction relative to the support housing, whereby the distal end of the support housing projects over the activating sleeve,
    a cartridge adapted to retain medicine to be administered in an injection procedure is mounted in the support housing,
    a first drive unit which is in active connection with the cartridge and the activating sleeve and can be triggered by means of the activating sleeve, a safety device, which secures the first drive unit prior to its activation by the activating sleeve for the injection procedure in position relative to the support housing, a needle arrangement, which is arranged ahead of the cartridge in the storage position of the injection device in the section of the distal end of the support housing, the needle arrangement comprising a cannula having distal and proximal needle ends arranged inside the support housing, the distal needle end being configured to pass through the opening defined by the front support housing part, a needle protection element which can be displaced from a non-active position into a position which covers the distal needle end projecting over the distal end of the support housing after the injection procedure, a second activatable drive unit, which displaces the needle protection element from the non-active position into the covering position, a seal stopper disposed in the opening defined by the front support housing part, a sealing element extending circumferentially between an external surface of the cartridge and an internal surface of the support housing in the connecting section, at least one throughput disposed in the connecting section between the front support housing part and the rear support housing part such that, in the first coupling position, there is a flow connection via the throughput between the front holding chamber and an outside of the support housing, and, in the second coupling position, the flow connection is interrupted between the front holding chamber and the outside of the support housing, wherein the needle protection element with the second drive unit cooperating therewith is arranged radially between the support housing and the activating sleeve.

2. The injection device according to claim 1, wherein the front support housing part grips over the rear support housing part in the connecting section of the coupling device.

3. The injection device according to claim 1, wherein the support housing parts in the first coupling position of the coupling device have a greater longitudinal extension relative to the second coupling position.

4. The injection device according to claim 1, wherein the coupling device on the two support housing parts comprises mutually cooperating locking elements configured such that the two support housing parts are locked respectively in the two coupling positions in an opposite direction of movement as viewed in the direction of the longitudinal axis and moving away from each other.

5. The injection device according to claim 1, wherein the front support housing part in the connecting section on a face side, which faces the rear support housing part and springs back in the direction of the longitudinal axis, comprises a shoulder which is wedge-shaped, as viewed in axial cross section, and designed to be continuous around the circumference of the front support housing part.

6. The injection device according to claim 1, wherein in the second coupling position of the two support housing parts the sealing element bears in a sealing manner against a back-springing face side or a shoulder arranged on the back-springing face side, and also access into the front holding chamber is interrupted by the throughput.

7. The injection device according to claim 1, wherein the rear support housing part on its external surface and in the region of its proximal end has at least two detent noses spaced apart in the direction of the longitudinal axis, which interact with a detent element arranged on the activating sleeve, such that the detent noses define relative positions of the support housing and the activating sleeve relative to one another on the one hand in the storage position and on the other hand in the injection position, and in that only a relative longitudinal displacement of the activating sleeve relative to the support housing is permitted from the storage position to the injection position, but a relative longitudinal displacement in the opposite direction is prevented.

8. The injection device according to claim 1, wherein the activating sleeve in the region of the distal end of the support housing and on its internal surface comprises a stop surface, which is aligned preferably at right angles to the longitudinal axis.

9. The injection device according to claim 1, wherein the needle protection element comprises a rocker-like lever element arranged with lever ends spaced apart from one another in the direction of the longitudinal axis, whereby the lever element in the storage position of the injection device has its distal-facing lever end supported on a stop element arranged on an external surface of the support housing.

10. The injection device according to claim 9, wherein the needle protection element comprises at its proximal end an elastically deformable safety element, which in the position of the needle protection element covering the needle arrangement is supported on a stop surface formed on an internal surface of the activating sleeve.

11. The injection device according to claim 1, further comprising a safety element adjacent to the needle protection element covering the needle arrangement and an adjusting element arranged on the support housing.

12. The injection device according to claim 11, wherein the adjusting element is designed to be continuous circumferentially and, in the position of the needle protection element covering the needle arrangement, the needle protection element is supported with its proximal end additionally on the adjusting element in the direction of the distal end of the support housing.

13. The injection device according to claim 1, wherein the needle arrangement comprises the cannula, a needle support arranged on the cannula and a guiding element mounting the needle support, whereby the guiding element is coupled with a cartridge end facing the distal end of the injection device and, in the storage position, the needle end of the cannula facing the cartridge end is arranged ahead of a cartridge seal which can be penetrated by the needle end.

14. The injection device according to claim 13, wherein the needle support is held axially displaceably in the guiding element and is secured in position on the guiding element in a storage position of the needle support by at least one releasable holding element relative to the guiding element.

15. The injection device according to claim 14, wherein an adjusting cam is arranged on the holding element, such that the cam projects over the holding element radially on a side opposite the longitudinal axis.

16. The injection device according to claim 1, wherein the first drive unit comprises a piston rod including a radially peripheral release designed as a depression, which is arranged in the storage position of the injection device in the region of a proximal end of the cartridge.

17. The injection device according to claim 1, wherein after releasing the safety device arranged at the proximal end and with a subsequent axial displacement of the activating sleeve relative to the support housing the first drive unit is triggered and the first drive unit displaces the cartridge together with the needle arrangement in the direction of the distal end of the support housing.

18. The injection device according to claim 1, wherein the support housing, at its distal end, comprises a control cam projecting in the direction of the longitudinal axis, which after a prespecifiable adjusting movement of the cartridge is in engagement with an adjusting cam arranged on a detachable holding element of a needle support, and thereby moves the detachable holding element into a release position.

19. The injection device according to claim 1, wherein a needle support is supported in the injection position on the distal end of the support housing and the needle support together with the cannula is displaced relative to a guiding element so far in the direction of a cartridge end closed by a penetrable cartridge seal, the proximal needle end of the cannula facing the cartridge is in flow connection with the medicine contained in the cartridge.

20. The injection device according to claim 1, wherein with the axial displacement of the activating sleeve relative to the support housing, the second drive unit cooperating with the needle protection element is released and thereby the needle protection element is shifted from a non-effective position into a position covering the distal needle end which projects over the distal end of the support housing after the injection procedure.

21. The injection device according to claim 1, wherein with the axial displacement of the activating sleeve relative to the support housing there is a simultaneous release of both the first and the second drive units.

22. The injection device according to claim 1, wherein the second drive unit comprises driving means supported with a distal-facing end section on a proximal facing end section of the needle protection element.

23. The injection device according to claim 1, wherein the safety device comprises a holding disc, which in the center of the holding disc comprises an opening as well as additionally adjoining radially outwards extending recesses for holding arms of the second drive unit to be secured to the holding disc in the storage position.

24. The injection device according to claim 1, further comprising a bacteria-tight casing for use during sterilization, the bacteria-tight casing surrounding other elements of the device and being gas-permeable for gassing with ethylene oxide.

25. The injection device according to claim 24, wherein prior to performing the sterilization thereof, the bacteria-tight casing is placed in a bath-like holding shell and in a region of a container edge the holding shell is sealed by means of a bacteria-tight cover which is still gas-permeable for gassing with ethylene oxide.

26. The injection device according to claim 24, wherein the bacteria-tight casing comprising a paper-fleece-like fiber functional textile made from thermally fused fibers of high density polyethylene (HDPE).

* * * * *